United States Patent [19]

Epstein et al.

[11] Patent Number: 5,304,126

[45] Date of Patent: Apr. 19, 1994

[54] INFUSION SYSTEM HAVING PLURAL FLUID FLOW LINES

[75] Inventors: Paul Epstein, Brookline; Harry Petschek, Lexington, both of Mass.; Eric LaWhite, South Royalton, Vt.; Clair Strohl, Norfolk, Mass.; Henry Coyne, Framingham, Mass.; Edward Kaleskas, Jefferson, Mass.; George Adaniva, Swampscott, Mass.

[73] Assignee: Abbott Laboratories, Abbott Park, Ill.

[21] Appl. No.: 636,059

[22] Filed: Dec. 31, 1990

Related U.S. Application Data

[60] Division of Ser. No. 355,035, May 16, 1989, Pat. No. 5,100,380, which is a continuation of Ser. No. 62,064, Jun. 11, 1987, abandoned, which is a continuation of Ser. No. 873,478, Jun. 11, 1986, Pat. No. 4,696,671, which is a continuation of Ser. No. 578,180, Feb. 8, 1984, abandoned.

[51] Int. Cl.⁵ .......................................... A61M 31/00
[52] U.S. Cl. ................................ 604/67; 128/DIG. 13
[58] Field of Search ............... 128/DIG. 12, DIG. 13; 604/65–67, 152, 158

[56] References Cited

U.S. PATENT DOCUMENTS

| | | | |
|---|---|---|---|
| 1,853,811 | 4/1932 | Hewitt . | |
| 2,027,588 | 1/1936 | Hannon | 128/227 |
| 2,672,051 | 3/1954 | Butler | 73/209 |
| 2,767,277 | 10/1956 | Wirth | 200/83 |

(List continued on next page.)

FOREIGN PATENT DOCUMENTS

| | | |
|---|---|---|
| 1034206 | 7/1978 | Canada . |
| 1110137 | 10/1981 | Canada .................. A61M 5/14 |
| 0013334A2 | 12/1979 | European Pat. Off. ...... A61M 5/14 |
| 0040592A2 | 5/1981 | European Pat. Off. ...... A61M 5/14 |
| 0096849A2 | 6/1983 | European Pat. Off. ...... A61M 5/14 |
| 3209721A1 | 3/1982 | Fed. Rep. of Germany ......... A61M 5/16 |
| 50-55198 | 5/1975 | Japan . |
| 52-86295 | 7/1977 | Japan . |
| 55-88768 | 7/1980 | Japan . |
| 55-105771 | 8/1980 | Japan . |
| 57-501268 | 7/1982 | Japan . |
| WO8202657 | 8/1982 | PCT Int'l Appl. ............ A61B 5/02 |

OTHER PUBLICATIONS

Edgerton, R. H., et al., "Multiplexer Unit for Controlled Infusion of Fluids," *Medical Research*, Aug.–Sep. 1969, pp. 17–19.

(List continued on next page.)

Primary Examiner—Lee S. Cohen
Assistant Examiner—John P. Lacyk
Attorney, Agent, or Firm—Weingarten, Schurgin, Gagnebin & Hayes

[57] ABSTRACT

An infusion system for administering multiple infusates at individually programmable rates, volumes, and sequences in any order from any one or more of plural fluid input ports through a patient output port and into the circulatory system of a patient. Infusates may be either continuously or time sequentially administered, and infusates may be either intermittently administered at selectively regular intervals or in time overlap to administer a dilution. Various error conditions are automatically detected and alarms generated in the event of conflicts between infusates, to identify times of no infusions, and to identify system malfunctions. The system is selectively operable, among others, in a priming mode, a maintenance mode, a normal-on mode, and a manual override mode. The system is operative to adapt actual to desired flow rates in normal operation. All fluids flow through a unitary disposable cassette without making any other system contact. Air bubbles in the fluid line are automatically detected and disposed of. Fluid pressures are monitored and system operation adjusted as a function of such pressures. Infusates may be administered from syringes as well as from standard bag or bottle containers. Infusate from a selected input port may be controllably pumped into a syringe for unsticking the syringe plunger. The system is selectively operable to adjust total fluid volume and rate to below preselected values for patients whose total fluid intake must be restricted. The system is operable to maintain an accurate record of total infusion history.

11 Claims, 14 Drawing Sheets

U.S. PATENT DOCUMENTS

| | | | |
|---|---|---|---|
| 2,880,909 | 4/1959 | Clymer et al. | 222/54 |
| 2,907,325 | 10/1959 | Burke | 128/214 |
| 3,543,752 | 12/1970 | Hesse | 128/214 |
| 3,559,644 | 2/1971 | Stoft | 128/214 |
| 3,566,930 | 3/1971 | Kirschner | 141/244 |
| 3,620,650 | 11/1971 | Shaw | 417/417 |
| 3,749,285 | 7/1973 | Latham, Jr. | 222/58 |
| 3,774,762 | 11/1973 | Lichtenstein | 210/94 |
| 3,798,982 | 3/1974 | Lundquist | 74/53 |
| 3,874,826 | 4/1975 | Lundquist et al. | 417/565 |
| 3,884,228 | 5/1975 | Hahn | 128/214 |
| 3,901,231 | 8/1975 | Olson | 128/214 |
| 3,912,455 | 10/1975 | Lichtenstein | 23/253 |
| 3,923,060 | 12/1975 | Ellinwood, Jr. | 128/260 |
| 3,946,731 | 3/1976 | Lichtenstein | 128/214 |
| 3,982,534 | 9/1976 | Buckman | 128/214 |
| 4,030,495 | 6/1977 | Virag | 128/214.2 |
| 4,037,598 | 7/1977 | Georgi | 128/214 |
| 4,056,333 | 11/1977 | Lundquist | 417/44 |
| 4,077,405 | 3/1978 | Haerten et al. | 128/214 F |
| 4,086,653 | 4/1978 | Gernes | 364/564 |
| 4,094,318 | 6/1978 | Burke et al. | 128/214 |
| 4,126,132 | 11/1978 | Portner et al. | 128/214 |
| 4,142,523 | 3/1979 | Stegeman | 128/214 R |
| 4,191,181 | 3/1980 | Franetzki et al. | 128/213 R |
| 4,191,183 | 3/1980 | Mendelson | 128/214 R |
| 4,191,184 | 3/1980 | Carlisle | 128/214 F |
| 4,204,538 | 5/1980 | Cannon | 128/214 R |
| 4,207,871 | 6/1980 | Jenkins | 128/214 R |
| 4,236,522 | 12/1980 | McDonald et al. | 128/419 PG |
| 4,236,880 | 12/1980 | Archibald | 417/478 |
| 4,261,356 | 4/1981 | Turner et al. | 128/214 R |
| 4,265,240 | 5/1981 | Jenkins | 128/214 E |
| 4,270,532 | 6/1981 | Franctzki et al. | 128/213 R |
| 4,276,004 | 6/1981 | Hahn | 417/479 |
| 4,282,872 | 8/1981 | Franetzki et al. | 128/213 R |
| 4,282,902 | 8/1981 | Haynes | 137/636.1 |
| 4,303,376 | 12/1981 | Siekmann | 417/360 |
| 4,308,866 | 1/1982 | Jelliffe et al. | 128/214 E |
| 4,316,460 | 2/1982 | Genese et al. | 128/214 R |
| 4,324,238 | 4/1982 | Genese et al. | 128/214 G |
| 4,336,800 | 6/1982 | Pastrone | 128/214 F |
| 4,373,527 | 2/1983 | Fischell | 128/260 |
| 4,391,598 | 7/1983 | Thompson | 604/65 |
| 4,391,600 | 7/1983 | Archibald | 604/153 |
| 4,392,847 | 7/1983 | Whitney et al. | 604/118 |
| 4,392,849 | 7/1983 | Petre et al. | 604/66 |
| 4,394,862 | 7/1983 | Shim | 604/67 |
| 4,395,259 | 7/1983 | Prestele et al. | 604/67 |
| 4,411,651 | 10/1983 | Schulman | 604/151 |
| 4,432,754 | 2/1984 | Urquhart et al. | 604/56 |
| 4,460,353 | 7/1984 | Deckert et al. | 604/31 |
| 4,464,170 | 8/1984 | Clemens et al. | 604/50 |
| 4,464,172 | 8/1984 | Lichtenstein | 604/65 |
| 4,468,219 | 8/1984 | George et al. | 604/66 |
| 4,468,222 | 8/1984 | Lundquist | 604/153 |
| 4,475,901 | 10/1984 | Kraegen et al. | 604/67 |
| 4,479,760 | 10/1984 | Bilstad et al. | 417/395 |
| 4,498,352 | 2/1985 | Hedelin | 74/568 R |
| 4,503,841 | 3/1985 | Tsukaya et al. | 128/4 |
| 4,512,764 | 4/1985 | Wunsch | 604/80 |
| 4,526,515 | 7/1985 | DeVries | 417/63 |
| 4,534,756 | 8/1985 | Nelson | 604/50 |
| 4,553,958 | 11/1985 | LeCocq | 604/67 |
| 4,559,036 | 12/1985 | Wunsch | 604/81 |
| 4,559,037 | 12/1985 | Franetzki et al. | 604/151 |
| 4,561,443 | 12/1985 | Hogrefe et al. | 128/419 PG |
| 4,563,173 | 1/1986 | Ledley | 604/81 |
| 4,613,325 | 9/1986 | Abrams | 604/65 |
| 4,624,661 | 11/1986 | Arimond | 604/151 |
| 4,685,903 | 8/1987 | Cable et al. | 604/154 |
| 4,776,842 | 10/1988 | Franetzki et al. | 604/67 |

OTHER PUBLICATIONS

Pipp, T. L., "Intravenous Infusion Pumps Justification and Selection and Utilization," *Infusion*, Mar./Apr. 1978, pp. 45-58.

Monahan, J. J., et al., "Intravenous Infusion Pumps-an added dimension to perenteral therapy," *American Journal of Hospital Pharmacy*, Jan. 1972, pp. 54-59.

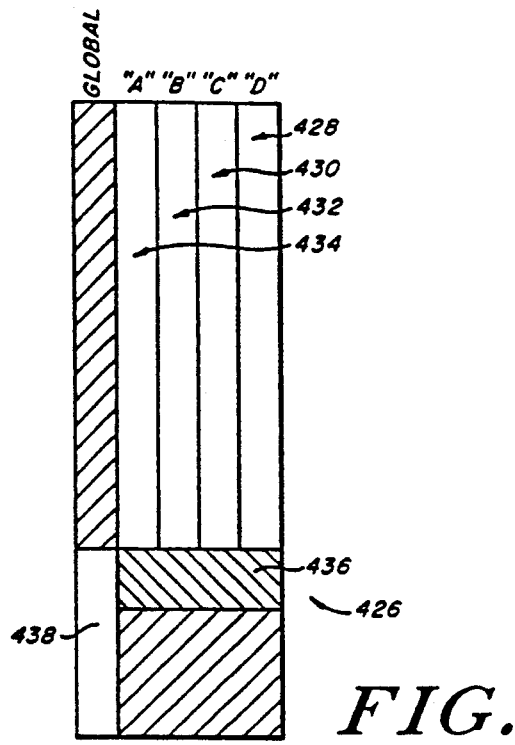
FIG. 11
| 7 | 6 | 5 | 4 | 3 | 2 | 1 | 0 |
|---|---|---|---|---|---|---|---|
| X-STATE | | X ERR | Y-STATE | | Y ERR | CNTL | |
| STATE | 0 | 1 | WAITING TO EXECUTE |
|---|---|---|---|
| | 1 | 0 | EXECUTING |
| | 1 | 0 | READY FOR NEW INST. |
| | 0 | 0 | VIRGIN WAKEUP |
| CNTL | 0 | 0 | CONTINUE |
| | 1 | 1 | STOP |
450
FIG. 13A
| 7 ABORT | 6 X/Y | 5 READ/WRITE | 4 NORM/OTHER | 3 D0-D7 C4 | 2 V1-V6 | 1 ALL | 0 | |
|---|---|---|---|---|---|---|---|---|
| 1. 1 | X=1 Y=0 | — | — | — | — | — | 0 | ABORT X OR Y |
| 2. 0 | " | 1 | 1 | 0 | 0 | 0 | 0 | READS (STATUS BYTE) |
| 3. 0 | " | 1 | 0 | 1 | 0 | 0 | 0 | READ D0→D7 |
| 4. 0 | " | 1 | 0 | 0 | 1 | 0 | 0 | READ V0→V6 |
| 5. 0 | " | 1 | 0 | 0 | 0 | 1 | 0 | READS, D0→D7, V0→V6, C0→C4 |
| 6. 0 | " | 0 | 1 | 0 | 0 | 0 | 0 | WRITE C0→C3, READ D0→D2 |
| 7. 0 | " | 0 | 0 | 1 | 0 | 0 | 0 | WRITE C4, READ (OPSI) D3 |
| 8. 0 | " | 0 | 0 | 0 | 1 | 0 | 0 | D0, ØPSI MEASUREMENT |
448
FIG. 12
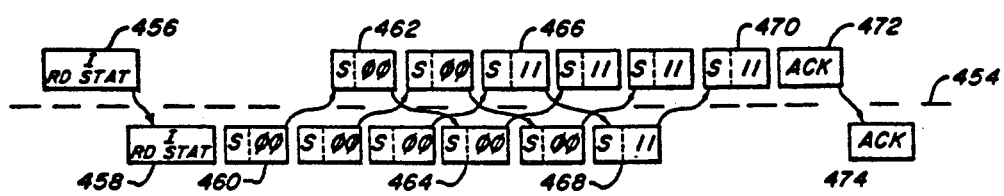
FIG. 13B

| | 7 | 6 | 5 | 4 | 3 | 2 | 1 | 0 |
|---|---|---|---|---|---|---|---|---|
| $C_0$ | PUMP PRIME | \multicolumn{6}{c|}{(MICROSTROKES/PUMP STROKE)} | $2^0$ |

476

| | 15 | 14 | 13 | 12 | 11 | 10 | 9 | 8 |
|---|---|---|---|---|---|---|---|---|
| $C_1$ | $T_2$ | $T_1$ | $T_0$ | | | | | |

478

| | 7 | 6 | 5 | 4 | 3 | 2 | 1 | 0 |
|---|---|---|---|---|---|---|---|---|
| $C_2$ | \multicolumn{8}{c|}{(TIME/PUMP STROKE)} |

480

| | 7 | 6 | 5 | 4 | 3 | 2 | 1 | 0 |
|---|---|---|---|---|---|---|---|---|
| $C_3$ | COLL PAT | $V_1$ | $V_0$ | \multicolumn{4}{c|}{$2^4$ (PUMP STROKES)} | $2^0$ |

482

| | 7 | 6 | 5 | 4 | 3 | 2 | 1 | 0 |
|---|---|---|---|---|---|---|---|---|
| $C_4$ | \multicolumn{8}{c|}{MAXIMUM OCCLUSION PRESSURE} |

| $D_0$ | BOTTLE HEIGHT PRESSURE (P2) | — 488 |
| $D_1$ | AIR IN LINE Δ (P4, P3) | — 490 |
| $D_2$ | VOLUME CORRECTION (N2, N1) | — 492 |
| $D_3$ | ZERO PSI (0 PSI) | — 494 |
| $D_4$ | MATCH PRESSURE (P3) | — 496 |
| $D_5$ | PATIENT PRESSURE (P5) | — 498 |
| $D_6$ | ERROR FIELD | — 500 |
| $D_7$ | ERROR FIELD | — 502 |

FIG. 15

INFUSION SYSTEM HAVING PLURAL FLUID FLOW LINES

This application is a division of application Ser. No. 07/355,035, filed May 16, 1989, entitled REMOTELY PROGRAMMABLE INFUSION SYSTEM now U.S. Pat. No. 5,100,380; which is a continuation of Ser. No. 07/062,064, filed Jun. 11, 1987 now abandoned; which is a continuation of Ser. No. 06/873,478, filed Jun. 11, 1986, now U.S. Pat. No. 4,696,671; which is a continuation of Ser. No. 06/578,180, filed Feb. 8, 1984, now abandoned; and this application is related to Ser. No. 07/039,154, now U.S. Pat. No. 4,828,545, which is also a division of U.S. Pat. No. 4,696,671; and Ser. No. 07/382,719, which is also a continuation of Ser. No. 07/355,035.

FIELD OF THE INVENTION

This invention is directed to the field of surgery, and more particularly, to a novel infusion system having plural fluid input ports and at least one patient output port.

BACKGROUND OF THE INVENTION

Intravenous infusion therapy is prescribed where it is desirable to administer medications and other fluids directly into the circulatory system of a patient. It is estimated that approximately forty percent of U.S. hospital patients presently receive some form of infusion therapy and it is expected that the proportion will grow in the future due to the improved health care that results from such therapy.

For many clinical procedures, it is desirable to intravenously administer several fluids to a patient. Plural independent gravity flow controllers and plural independent electronic pumps have heretofore been employed for this purpose. The plural gravity flow controllers, however, are disadvantageous, among other things, due to the increased possibility of infection occasioned by multiple IV venipuncture; due to the flow inaccuracies occasioned, among other things, by patient movement induced tube occlusion or tubing shape changes; due to the considerable labor and time required from a nurse or other health practioner to manually control the plural gravity flow controllers in accordance with a prescribed course of therapy; due to clutter around the patient; and due to the possibility of out-of-control infusion occasioned by a failure of one or more of the gravity flow controllers. The plural independent pumps are disadvantageous, among other things, due to the clutter around the patient occasioned by the use of plural pumps; due to the increased possibility of infection occasioned by multiple IV venipuncture; due to the comparatively high cost of procuring and maintaining several pumps for each such patient; due to the incapability of the heretofore known pumps to administer more than two infusates in time sequence without additional pumps; due to the incapability of the heretofore known pumps to administer dilutions; due to the considerable time and labor required by the health practioner to program and to supervise the plural independent pumps; and due to the comparatively high cost incurred in maintaining an inventory of tubes and administration sets that must be replaced periodically to avoid infection for each pump, fluid, and patient, often amounting on an annual basis to about one half the cost of the pumps themselves.

SUMMARY OF THE INVENTION

The novel infusion system of the present invention contemplates means operable to controllably infuse preselected fluids from any one or more of plural fluid input ports either simultaneously or in time sequence through at least one patient output port and into the circulatory system of a patient in a predetermined time sequence. Infusates may be administered from bag or bottle containers or from syringes. A small quantity of fluid may be pumped into the syringe to unstick the syringe plunger. The infusion system of the present invention is operative to identify potentially conflicting infusions and to alert the system operator. The system operator may, among other things, either reschedule conflicting infusions or select an alarm and automatic shutdown prior to the time when conflicting infusions are scheduled to commence. The infusion system of the present invention is operative to administer nonconflicting infusions at the same rate or different rates to provide either mixing of the infusates or dilution of the concentration of one of the infusates.

The infusion system of the present invention is selectively operative in a maintenance mode to controllably administer a fluid from a preselected fluid input port to keep the vein of a patient open at such times when selected fluids are not being infused in accordance with a particular course of infusion therapy.

The infusion system is selectively operable in a priming mode to vent fluid and air from a selected fluid input port to prevent possible air embolism.

The infusion system is selectively operable in a manually initiated override mode to controllably administer any one or more of plural fluids during emergency or other situations.

The infusion system having plural fluid input ports and at least one patient output port of the present invention in preferred embodiment includes a processor. A memory is operatively coupled to the processor. Means coupled to the processor are provided for entering into the memory data representative both of the desired time sequence for and of a desired rate of flow of each of any one of a plurality of fluids to be infused in any order. A plurality of input valves are operatively connected to the processor for accessing the flow of a corresponding one of the fluid inputs. An output valve is operatively connected to the processor for controlling the fluid flow of the output port. A pumping chamber is operatively connected to the processor and is in fluid communication with each of the input valves and the output valve along a common fluid flow path. Means coupled to the processor and responsive to the data are provided for repetitively actuating the input valves and concurrently expanding the pumping chamber in a time sequence selected to fill the pumping chamber with the corresponding fluid to be infused and for repetitively actuating the output valve and concurrently contracting the pumping chamber at a rate selected to infuse the corresponding fluid through the patient output line at the desired rate. The data entry means includes an operator interactive display and a keyboard. The processor includes a main control processor and a pump control processor slaved to the main control processor. The main control processor is operative to provide operator prompts on the operator interactive display, to provide system status information on the display, and to provide one of plural display templates representative of desired pumping mode and sequence. The pump control processor executes instructions representative of the desired pumping sequence and mode that are down loaded thereto by the main control processor for execution, generates and reports various error and alarm conditions to the main control processor, and generates several alarms including air in line, patient occlusion, and empty bottle. The pumping chamber and the input and output valves are provided in a sterile, disposable, cassette injection-molded out of biologically inert medical-grade plastic. The cassette includes a longitudinally extending channel in fluid communication with the pumping chamber, a pressure chamber, a plurality of fluid input ports, a patient output port, and a vent port. The cassette in preferred embodiment consists of a two part semi-rigid housing and a flexible diaphragm consisting of silicone rubber that is sandwiched between the two parts of the housing. The diaphragm includes a plurality of resilient valve stops that individually project into a corresponding one of the fluid input ports, output port, and vent port, and includes a flexible drum that extends over the pressure chamber and a dome that extends over the pumping chamber. The cassette is oriented preferably at a forty-five degree angle to the vertical with the vent port and pressure chamber above the pumping chamber. Any slight quantity of air in the fluid flow path rises above the pumping chamber and into the pressure chamber thereby preventing the possibility of air passing to the patient. A stepper-motor controlled cam drives a corresponding spring-biased plunger associated with each input fluid port and the output port for controlling the state of actuation of its associated resilient stop. The input and output port plungers are so driven that the patient output port is in a closed state whenever any one of the fluid input ports are in an open state and are so driven that all of the input ports are closed whenever the output is open, to prevent unintended gravity flow infusion. A stepper-motor controlled cam strokes a pumping piston associated with the pumping chamber to expand or contract the pumping chamber for filling or expelling fluid therefrom. A pressure transducer is coupled to the pressure chamber and operatively connected to the pump controller for providing pressure data during each pumping piston stroke representative of air-in-line, bottle head pressure, downstream occlusion, and of variation between actual and intended infusate volume. The system responds to the pressure data to vent fluid and air from the line and to adjust operation in a pressure dependent manner. The system is selectively operable in a controlled mode to allow fluid to flow from any selected fluid input to a selected output under gravity control without actuating the pumping piston whenever desirable.

BRIEF DESCRIPTION OF THE DRAWINGS

Other features and advantageous of the present invention will become apparent as the invention becomes better understood by referring to the following exemplary and non-limiting detailed description of the preferred embodiment, and to the drawings, wherein:

FIG. 11 is a diagram illustrating a data file of the main control processor of the infusion system having plural fluid input ports and at least one patient output port according to the present invention;

FIG. 12 is a diagram illustrating an instruction byte of the main control processor of the infusion system having plural fluid input ports and at least one patient output port according to the present invention;

FIG. 13 illustrates in FIG. 13A a status byte of the pump control processor and in FIG. 13B a communications protocol between the main control processor and the pump control processor of the infusion system having plural fluid input ports and at least one patient output port according to the present invention;

FIG. 14 illustrates the command bytes of the main control processor of the infusion system having plural fluid input ports and at least one patient output port according to the present invention;

FIG. 15 illustrates the data bytes of the pump control processor of the infusion system having plural fluid input ports and at least one patient output port according to the present invention;

DETAILED DESCRIPTION OF THE PREFERRED EMBODIMENT

Figure 1:
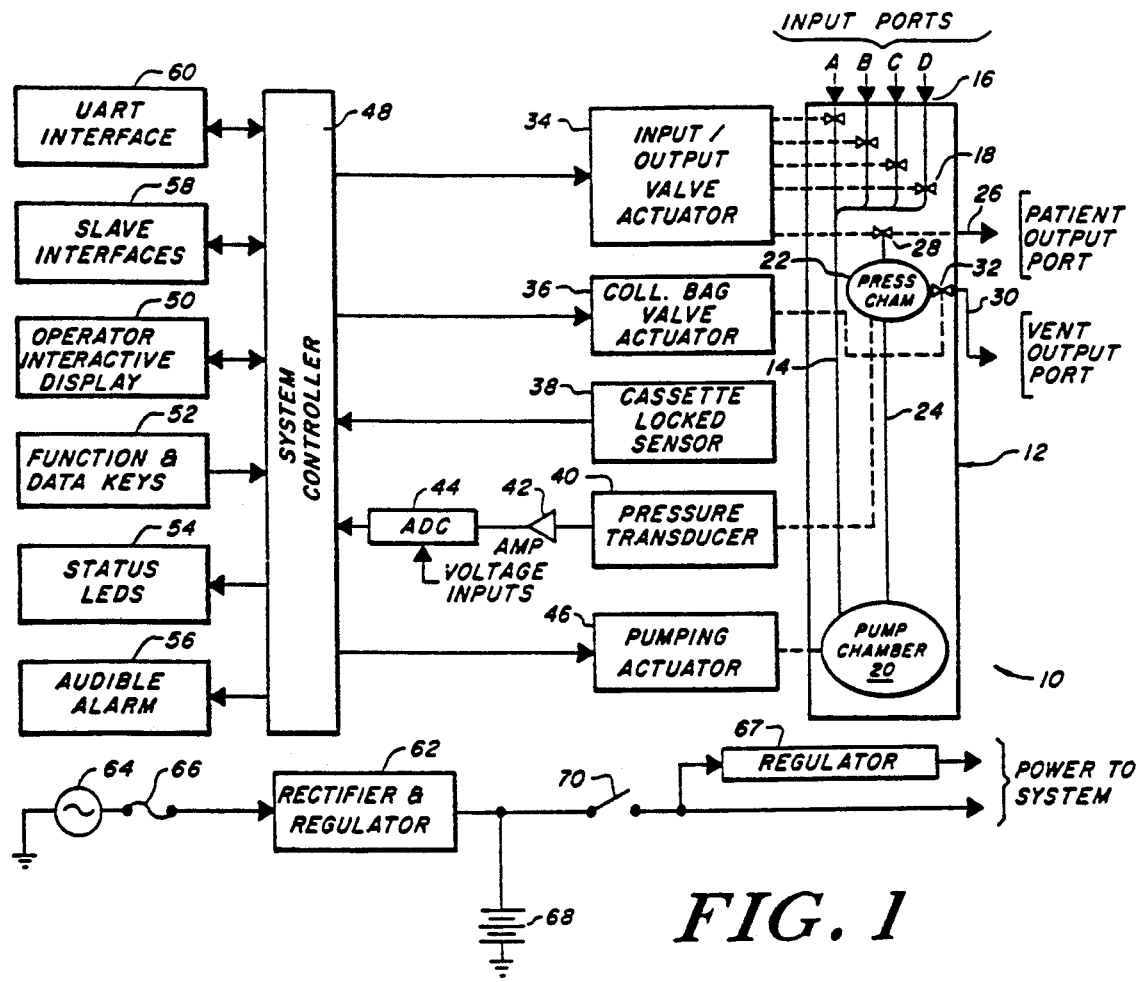
FIG. 1 is a block diagram illustrating the novel infusion system having plural fluid input ports and at least one patient output port according to the present invention.

Referring now to FIG. 1, generally designated at 10 is a block diagram of the novel infusion system having plural fluid input ports and at least one patient output port according to the present invention. The system 10 includes a disposable cassette generally designated 12 to be described having a fluid channel 14. A plurality of fluid input ports 16, four (designated "A", "B", "C", and "D") being specifically illustrated, are connected to the fluid flow channel 14 through a corresponding one of a plurality of valves 18. Each fluid input port 16 is directly connectable to a selected fluid to be infused, not shown. The cassette 12 includes a pumping chamber generally designated 20 connected to the fluid channel 14, and a pressure chamber generally designated 22 connected to the pumping chamber 20 via a fluid flow channel 24. A patient output port 26 is connected in a fluid flow path to the pressure chamber 22 via a valve 28, and a vent output port 30 is connected to the pressure chamber 22 in a fluid flow path via a valve 32. The patient output port 26 is directly connectable to a patient via a patient output line, not shown. The vent output port 30 is directly connectable, for example, to a collection bag to be described or other fluid sink.

An input and output valve actuator 34 to be described is operatively connected to the plural fluid input valves 18 and to the patient output valve 28. The actuator 34 is operative to select the "open" and the "closed" state of the valves 18, 28, and therewith to control fluid flow from the corresponding fluid input ports 16 into the cassette 12 and to control fluid flow out of the cassette into the patient. The actuator 34 is preferably operative to prevent the input and output valves from being simultaneously in the "open" condition to eliminate the possibility of unintended gravity flow infusion. A separate actuator to be described is preferably connected to the output valve 23 to maintain the patient output port and any selected input port "open".

A vent valve actuator 36 to be described is operatively connected to the vent valve 32. The actuator 36 is operative to select the "open" and the "closed" state of the valve 32, and therewith to control fluid flow from the cassette 12 into the collection bag to remove air from the fluid flow channel during initial setup and during operation of the infusion system.

A cassette-locked-in-place sensor 38 is operative to provide a signal that represents that the cassette is in its intended operating position to prevent fluid leakage and unintended infusion.

A pressure transducer 40 to be described is operatively connected to the pressure chamber 22. The pressure transducer 40 is operative to provide an analog signal representative of the pressure in the pressure chamber 22. An amplifier 42 amplifies the analog signal, and an analog to digital converter (ADC) 44 converts the amplified analog signal into digital data. During preselected stages of a pumping sequence to be described, the digital data provides information representative of air in line, of actual infusion volume relative to nominal infusion volume, of patient output line occlusion, and of fluid level remaining to be infused through corresponding fluid input ports 16.

A pumping actuator 46 to be described is operatively connected to the pump chamber 20. The pumping actuator 46 is operative to controllably fill and pump fluid from the pumping chamber 20 into either the patient output port 26 or the vent output port 30 in dependence on the state of actuation of the valves 28 and 32. The pumping actuator 46 is operative to precisely administer an intended amount of fluid in an intended time interval from any one or more of the fluid input ports 16 in any order either in time sequence or in time overlap to dilute the concentration of a selected infusate.

A system controller generally designated 48 to be described is operatively connected to the input and output valve actuator 34, to the vent valve actuator 36, to the cassette-locked-in-place sensor 38, to the analog to digital converter 44, and to the pumping actuator 46. The system controller 48 is operative to provide control signals to the actuator 34 to "open" and "close" the valves 18 in an intended time sequence, to provide control signals to the actuator 46 to pump the chamber 20 at a rate selected to administer a preselected volume of infusate during a prescribed time interval, and to provide control signals to the actuator 36 to eliminate air from the fluid flow path during set-up and during infusion.

An operator interactive display 50 is operatively connected to the system controller 48. The display 50 is operative to display one of plural display templates to be described that individually correspond to the modes of operation of the system controller 48, to display system status information, to display operator prompts to assist the operator in selecting volume, rate, and time of infusion, and to display various error and alarm conditions. The modes includes a flush mode template, a prime mode template, an override mode template, a primary mode template, and a piggyback mode template.

Operator data and function keys 52 to be described are operatively connected to the system controller 48. The data and function keys 52 are operative for selecting the rate, volume, and time of infusion; for selecting the state of operation of the infusion system including the override mode, the priming mode, and the normal-on mode; for controlling the operator interactive display; and for selecting maximum occlusion pressure, minimum infusion rate, and total fluid volume to be administered.

Status light emitting diodes (LED's) 54 are operatively connected to the system controller 48. The LED's 54 are operative to provide a visual indication of the various alarm conditions and of battery status. An audible alarm 56 is operatively connected to the system controller 48 to provide an audible indication of alarm condition. One or more slave interfaces 58 are operatively connected to the system controller 48. Each slave interface 58 is connectable to an auxiliary pump to be described that may be slaved to the system controller 48 to administer the infusion of an incompatible infusate. A universal asynchronous receiver transmitter interface (UART) 60 is operatively connected to the system controller 48. The UART 60 may be connected to any suitable peripheral device such as a display terminal or a computerized central nurse station.

A rectifier and regulator 62 is connected to a source of AC power 64 such as a conventional hospital outlet via a fusible link 66. A regulator 67 is connected to the rectifier and regulator 62 via a switch 70. The rectifier and regulator 62 and regulator 67 provide power to the infusion system in normal operation. A battery 68 provides power to the infusion system either in the event of a power failure or in the event that it is desirable to move the patient such as between an intensive care unit and an operating room. The battery 68, the rectifier and regulator 62, and regulator 67 are operatively connected to the ADC 44 designated "Voltage Inputs". The system controller 48 is operative in response to a fall in the output of the converter signal from the regulators below a predetermined value to switch to the battery 68, and the controller 48 is operative to activate a corresponding status LED to provide a low battery indication whenever the level of the battery falls below a predetermined level.

Figure 2:
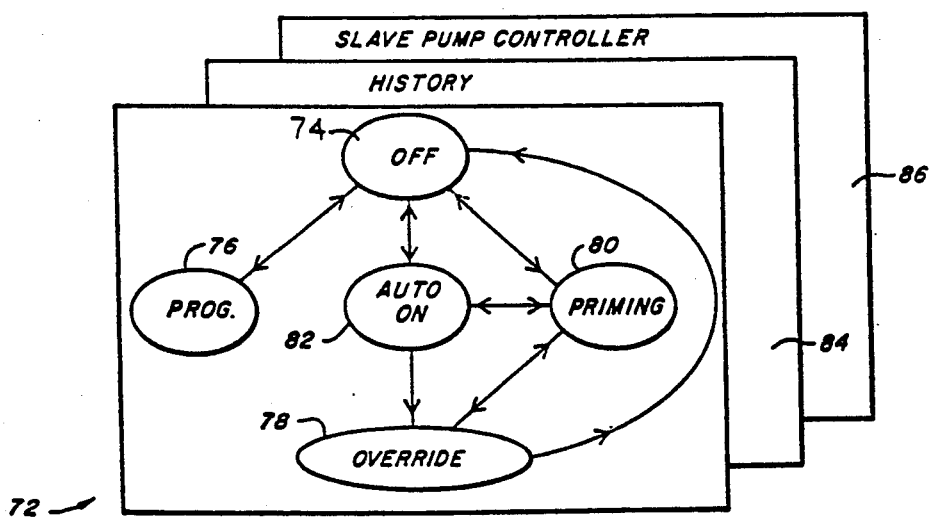
FIG. 2 is a state diagram illustrating the operating states of the infusion system having plural fluid input ports and at least one patient output port according to the present invention.

Referring now to FIG. 2, generally designated at 72 is state diagram illustrating the principal operating states of the system controller 48 (FIG. 1). In an "off" state 74, the system controller 48 is waiting, its clock is running, and no pumping is occurring. In a "programming" state 76, data is selectably input to specify the time, rate, and volume for fluid to be administered from any one or more of the plural fluid input ports 16 (FIG. 1), and data is selectably input to specify current time, KVO rate, maximum occlusion pressure, and total fluid rate and volume. Data entered is selectably displayable in the "programming" state on the operator interactive display for operator review. In an "override" state 78, the system controller 48 (FIG. 1) is operative in a manual override mode. In the state 78, data is selectably input to specify an emergency infusion rate from a selected one of the plural fluid input ports and to pump the fluid at the specified emergency rate. In a "priming" state 80, data is selectably input to specify an input line as a priming line. The system controller is operative in the "priming" state to allow fluid to flow by gravity from a selected input port through the cassette 12 (FIG. 1) and either into the collection bag to remove air from the cassette or through the output port and into the patient output line prior to venipuncture to remove air from the patient line. In the "priming" state, fluid may also be primed by pumping. In an "auto-on" state 82, the system controller is operative to automatically pump fluid from the input ports at the rates, volumes, and times specified in the "programming" state. The system controller in the "programming" state for a particular one of the plural fluid input ports may also be in the "auto-on" state 82 for the other ones of the plural fluid input ports that may be being infused at a selected rate, volume, and time into the patient in accordance with a desired course of therapy. In a "history" state 84, the system controller is operative to display on the operator interactive display data representative of the total quantity of fluid administered to a patient from the plural fluid input ports at a given time. Data accumulated in the history state 84 can advantageously be employed with a computerized hospital information system. In a "slave pump controller" mode 86, the system controller is operative to control one or more auxiliary pumps. The auxiliary pumps can advantageously be employed to control one or more additional infusions for the administration of an incompatible drug without losing the benefit of integrated infusion control and data accumulation.

Figure 3A:
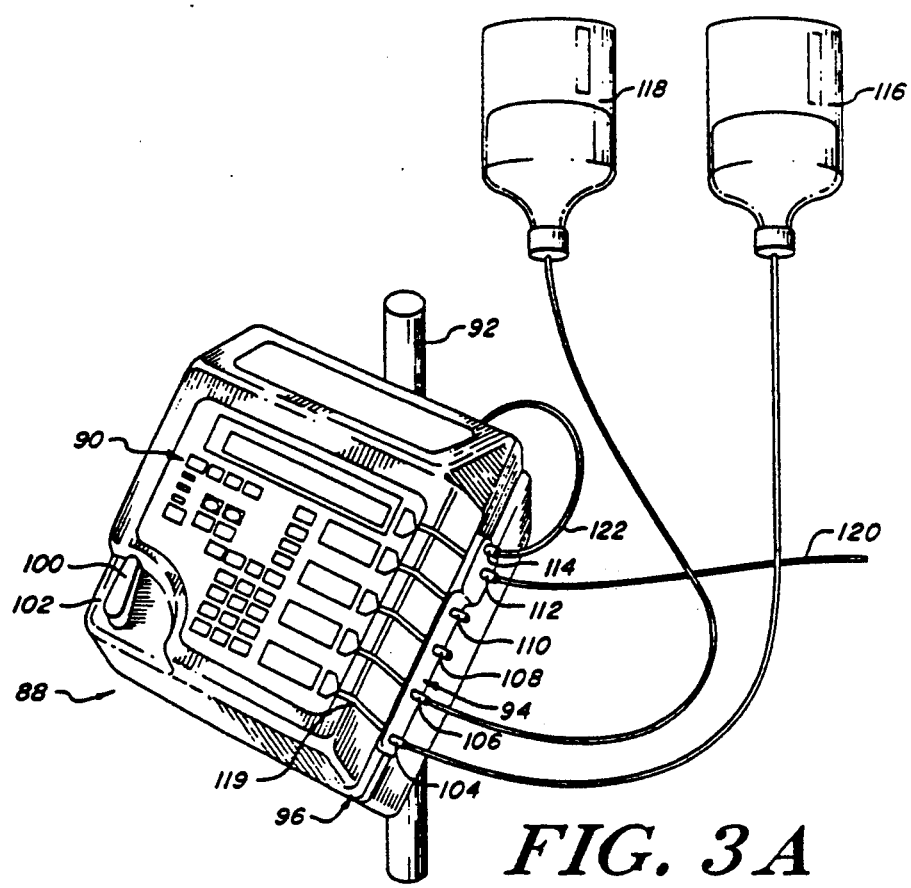
FIG. 3 illustrates in FIG. 3A an isometric view of a preferred embodiment of a housing for, and illustrates in FIG. 3B a plan view of a preferred embodiment of a control panel for, the infusion system having plural fluid input ports and at least one patient output port according to the present invention.

Referring now to FIG. 3A, generally designated at 88 is an isometric view illustrating a preferred embodiment of a housing of the infusion system having plural fluid input ports and at least one patient output port according to the present invention. The housing 88 is mounted to a conventional IV pole 92 such that its front panel generally designated 90 to be described is oriented at an angle selected to provide ease of operator access, preferably 45°. A disposable cassette generally designated 94 to be described is slidably mounted in a channel generally designated 96 provided therefor on one side of the housing 88. The cassette 94 is oriented at the same angle of inclination to the vertical to allow both pumping with slight quantities of air in the fluid flow path and the expeditious removal of air from the fluid flow path as appears more fully below. A locking lever 100 having a safety mechanism 102 to be described is pivotally mounted to the housing 88. The lever 100 is operatively connected to a rod to be described that is mounted for reciprocating motion in the housing 88. By simultaneously releasing the locking mechanism 102 and pivoting the lever 100, the rod is operate to removably retain the cassette 94 in the channel 96 on the side of the housing 88 in a manner to be described. The cassette 94 includes four fluid input ports 104, 106, 108, and 110, a patient output port 112, and a vent output port 114. A plurality of fluid containers are positioned a predetermined vertical distance above the housing 88 and directly connected to corresponding of the fluid input ports, two such fluid containers 116, 118 connected to the input ports 104, 106 being specifically illustrated. It will be appreciated that two additional fluid containers, bags, or syringes, not shown, may be directly connected to the ports 108, 110. A plurality of indicating lines 119 are provided on the side of the housing. A patient output line 120 is connected to the output port 112, and a collection bag line 122 is connected between the vent output port 114 and a collection bag removably retained on the back of the housing 88, not shown.

Figure 3B:
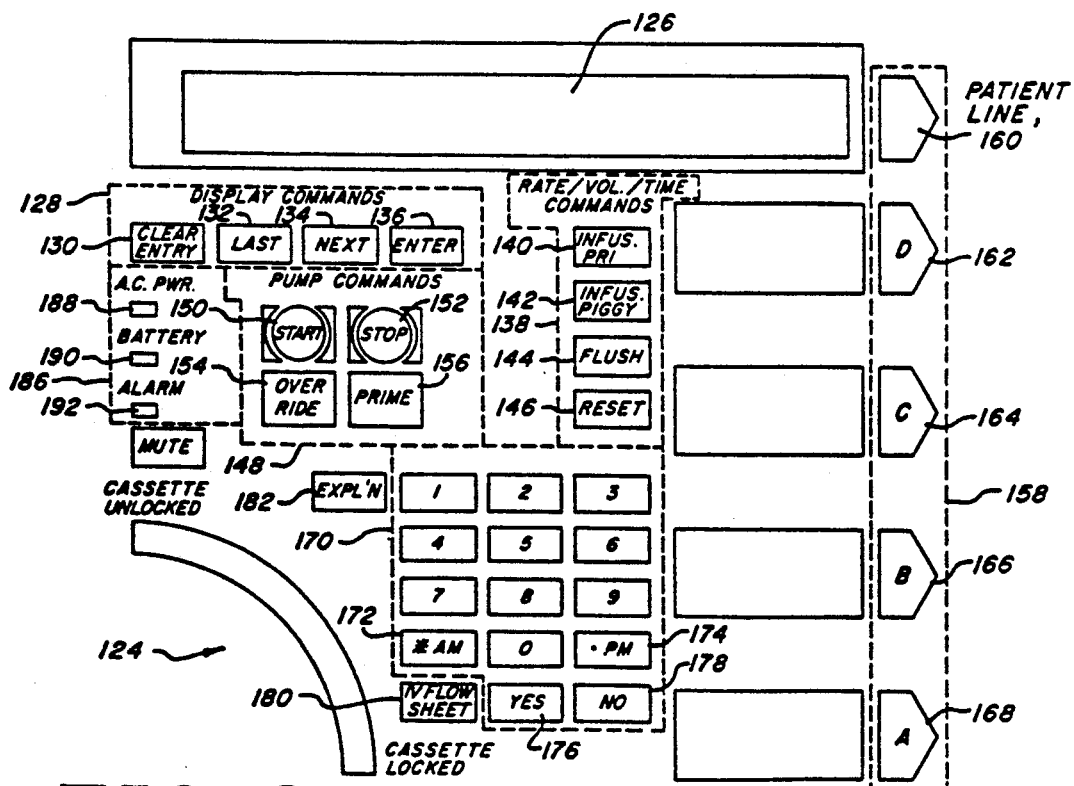

Referring now to FIG. 3B, generally designated at 124 is a plan view of a preferred embodiment of the front panel of the housing of the infusion system having plural fluid input ports and at least one patient output port according to the present invention. The front panel 124 includes an operator interactive display 126 for displaying one of a plurality of display templates to be described. The display 126 preferably is an 80 character LCD display commercially available, for example, from Epson. A plurality of display command keys designated by a dashed box 128 are provided on the front panel 124. The display keys 128 include a clear entry key 130, a last entry key 132, a next entry key 134, and an enter key 136. The clear entry key 130 when pressed clears inadvertently or mistakenly entered data, the last entry key 132 when pressed moves a display cursor to a previous field of a display, the next entry key 134 when pressed moves a display cursor to the next field of a display, and the enter key 136 enters the data entered into the various fields of a display into system memory.

A plurality of rate, volume, and time command keys designated by a dashed box 138 are provided on the front panel 124. The rate, volume, and time command keys 138 include a primary infusion key 140, a piggyback infusion key 142, a flush key 144, and a reset key 146. The primary infusion key 140 when pressed selects the programming state 76 (FIG. 2), and displays a primary infusion template for each fluid input that allows selection of the rate, volume, and time sequence of infusion from any one or more of the plural fluid input ports in any order to implement a prescribed course of therapy that calls for the nonsimultaneous infusion of primary fluids at the same or different rates in a predetermined time sequence. The primary infusion template preferably has the following format.

1. PRESS A, B, C, OR D TO PROGRAM LINE:__ CALL BACK Y/N?_"NEXT"

The operator then presses any one of keys 162, 160, 166, 168 to be described. If the operator selects the key 168, designated "A", for example, an "A" appears in the first data field of the primary infusion template. The operator then presses the "next" key 134 and the display cursor moves to the second data field of the infusion primary template. The operator then selects either a key 176 or a key 178 to be described and a "yes" or a "no" appears in the second data field of the template. Call back when selected by pressing the "yes" key 176 specifies that the system operator is to be called back prior to beginning infusion on the selected line. The operator then presses the "next" key 136 again and the system controller is operative to display the following display template.

2. LINE A RATE:__ML/HR INFUSE VOL:—ML FOR-HR-MIN CONTAINER:__ML "ENTER"

The operator then presses the appropriate data keys 170 to be described and appropriate display command keys 128 to enter a selected rate, volume, duration of fluid to be administered, and container volume for primary line "A". The data fields of the templates are shown herein by either "dashed" underline or by "solid" underline. "Dashed" underline entry is optional. For example, if rate and volume are specified for the above template, the system controller can calculate duration and volume. The operator then presses the "enter" key 136, and the selected data is entered into the corresponding addresses of a data file to be described for that line. The above process may be repeated for selecting the rate, volume, and time for lines B, C, and D as primary lines.

The piggyback infusion key 142, when pressed, selects the "programming" state 76 (FIG. 2) and displays a piggyback infusion template that allows selection of the rate, volume, and time sequence from any one or more of the plural fluid input ports in any order to implement a course of therapy that calls for the intermittent infusion of one or more piggyback fluids either at regular repeat intervals or in time overlap to provide a dilution of the concentration of one of the infusates. Piggyback infusions are each preferably less than sixty minutes in duration. The piggyback infusion template preferably has the following format.

3. PRESS A, B, C, OR D TO PROGRAM LINE:__ CALL BACK Y/N?_SYRINGE Y/N?_"NEXT"

The operator then presses any of keys 162, 164, 166, 168. If the operator selects the key 166, designated "B", for example, a "B" appears in the first data field of the piggyback infusion template. The operator then presses the "next" key 134 and the display cursor moves to the second data field of the piggyback infusion template. The operator then selects either the key 176 or the key 178 and a "yes" or a "no" appears in the second data field of the template. Call back again selects or calls back the operator before infusion on line "B". The operator then presses the "next" key 136 and the display cursor then moves to the third data field of the piggyback infusion template. The operator then selects either the key 176 or the key 178 and a "yes" or a "no" appears in the third data field of the template. Syringe when selected specifies a pumping sequence to unstick the syringe plunger from a preselected fluid input port in a manner to be described. The operator then presses the "next" key 136 again and the system controller is operative to display the following display template.

4. LINE B RATE:__ML/HR INFUSE VOL:__ML FOR__MIN Q:-HR X:__"NEXT"

The first data field allows the operator to select rate, the second data field allows the operator to select volume, the third data field allows the operator to select duration in minutes, the fourth data field designated "Q" allows the operator to select repeat interval, and the fifth data field designated "X" allows the operator to select the number of times the same infusion is to be repeated. It is noted that the repeat interval for this template is optional. After entering the data into the data fields and pressing the "next" key, the system controller is then operative to display the following display template.

5. B CONTAINER:__ML DILUTE WITH LINE— DILUENT VOL:—ML RATE:—ML/HR "ENTER"

The first data field allows the operator to specify the volume of the fluid container for the "B" line, the second data field allows the operator to select a fluid input line for dilution, the third data field allows the operator to select diluent volume, and the fourth data field allows the operator to select diluent rate. The operator then presses the "enter" key 136 and the data is written into the corresponding address locations of the data file for that line.

The flush key 144 when pressed is operative to allow the selection of one of the plural fluid input ports as a flushing line for buffering one infusate from another and to allow the selection of a variable flush quantity and rate selected to accommodate different lengths of the patient output line 120 (FIG. 3A). The flush display template preferably has the following format.

6. FLUSH PATIENT LINE WITH LINE__RATE__ML/HR VOL:__ML/FLUSH "ENTER"

The operator then presses a selected key 162, 164, 166, 168 to specify the flush line for the first data field, and the appropriate keys 170 to specify the rate and volume of flush for the second and third data fields. The operator then presses the "enter" key and the data is entered into the data file. During flushing, the system controller is operative to display the following display template.

7. FLUSHING PATIENT LINE WITH LINE__ __ML FLUSHED TILL NOW

The reset key 146 when pressed allows the operator to clear a previous rate, time, and volume selection for each of the plural fluid input ports. If an infusion is in process when this key is pressed, the system controller is operative to display on the operator interactive display 128 the following display template to prompt the operator to insure that the key has not accidently been pressed.

8. RESET LINE- "ENTER"

A plurality of pump command keys designated by a dashed box 148 are provided on the front panel 124. The pump command keys 148 include a start key 150 when pressed is operative to initiate a selected course of infusion therapy. The system controller is operative to display the following template if the start key 150 is pressed for a primary line.

9. START LINE__ __PM-HR-MIN FROM NOW OR AFTER LINE-INFUSION COMPLETE "ENTER"

The first and second data fields of the start primary display template allows operator selection of the starting time of the selected line in machine time, the third and fourth data fields allows operator selection of a specified time delay start, and the fifth data field allows operator selection of a start of the designated primary line after termination of infusion on another line. The operator then presses the "enter" key and the selected data is written into the data file address locations for that line.

The system controller is operative to display the following display template if the start key 150 is pressed for a piggyback line.

10. START LINE__ __:__AM-HR-MIN FROM NOW "ENTER"

The first data field allows operator selection of the line. The second and the third data fields (hours, minutes) allow operator selection of a specified starting time. The fourth and fifth data fields allow operator selection of specified time delay start before the selected line is started. If no data is entered there, pumping starts at current system time. The operator then presses the "enter" key and the selected data is written into the data field address locations for that line.

The stop key 152 when pressed is operative to terminate the desired course of infusion. The system controller is operative to display the following display template to ensure an intended stop.

11. STOP LINE- "ENTER"

The data field for the display template allows operator selection of the appropriate line to be stopped, which, when entered, is written to the data file.

The override key 154 when pressed is operative to select the override state 78 (FIG. 2). The override key 154 stops all previously selected infusion parameters and allows the operator to select any one of the fluid input ports at a selected rate for infusion during emergency or other situations. The system controller is operative to display the following template when the key 154 is pressed.

12. OVERRIDE LINE__WITH NEW RATE__ML/HR STOPS ALL PROGRAMMED LINES "ENTER"

The first data field allows operation selection of the override line, and the second data field allows operator selection of the override rate. The display template advises the operator with a prompt that all previously selected rates, lines, and volumes are no longer in effect.

The prime key 156 when pressed selects the priming state 80 (FIG. 2). The priming key 156 allows the operator to select any one of the fluid input ports to allow fluid to flow from the selected port through the cassette and into either the collection bag or patient output line. The corresponding valves are held open allowing fluid to flow as long as the selected line key is held down. The system controller is operative to display the following display template when the prime key is pressed.

13. PRESS & HOLD DOWN KEY TO PRIME LINE-INTO COLLECTION BAG "ENTER"

The first data field allows the system operator to select which input port is to be primed into the collection bag. The system controller is operative to continue the priming action from the selected line so long as the corresponding one of the keys 162, 164, 166, and 168 is manually maintained in a closed condition.

If the system operator presses the key 160 after pressing the prime key, the system controller is operative to display the following display template.

14. PRESS & HOLD DOWN KEY TO PRIME LINE-INTO PATIENT LINE "ENTER"

The first data field of the template allows the operator to select which input port is to be primed into the patient line. The system controller is operative to prime the patient line as long as the corresponding key 162, 164, 166, and 168 is held down.

A plurality of fluid input and output port control keys designated by a dashed box 158 are provided on the front panel 124. The input and output line selection keys 158 include a patient line key 160, a "D" input port selection key 162, a "C" input port selection key 164, a "B" input port selection key 166, and an "A" input port selection key 168. As described above, pressing the prime key 156 followed by pressing the patient line key 160 and with the selected line key held down, selects priming from the selected fluid input port through the cassette and into the patient output line so long as the selected line key is held down. Pressing the priming key followed by pressing any one of the keys 162, 164, 166, and 168 selects priming from the selected fluid input port through the cassette and into the collection bag. As described above, pressing the override key 154 and any one of the keys 162, 164, 166, and 168 selects operation in the override mode for the selected line. The keys 162, 164, 166, 168 are similarly operative when the primary infusion key 140, the piggyback key 142, and the flush key 144 are pressed.

If any one of the keys 162, 164, 166, 168 is pressed alone (that is, when not in combination with any key described above), the system controller is operative to display the status of the corresponding fluid input port using either a primary line or a piggyback line status display template. The primary line status display template preferably has the following format.

15. A: __ML/HR INFUSE VOL: -ML PRIMARY INFUSION CONTAINER VOL: __ML

The piggyback line status display template preferably has the following format.

16. D: __ML/HR INFUSE VOL: -ML Q: -X: __PIGGYBACK INFUSION CONTAINER VOL: __ML

If the key 160 is pressed alone (that is when not in combination with any key described above), the system controller is operative to display a patient line status template. The patient line status template preferably has the following format.

17. OCCLUSION PRES: __PSI MAX RATE: __ML/HR PATT LINE PRES: __PSI KVO RATE: __ML/HR

The first data field displays occlusion pressure, the second data field displays maximum rate, the third data field displays patient line pressure, and the fourth data field displays keep vein open (KVO) rate.

A plurality of data keys designated by a dashed box 170 are provided on the front panel 124. The data keys 170 include numeric keys "1" through "9" for entering the appropriate infusion parameters including rate, volume, and time for each of the plural fluid input ports, "AM" and "PM" keys to select the corresponding time periods, and "yes" and "no" keys 176, 178 to allow the operator to select among the operator prompts displayed in the various display templates on the operator interactive display 126.

An IV flow sheet key 180 is provided on the front panel 124. The key 180 when pressed is operative to select the history state 84 (FIG. 2). When the key 180 is pressed, the system controller is operative to display up-to-date total infusion volume. The system controller is operative to display the following display template when the key 180 is pressed.

| 18. | A:LOG | B:LOG | C:LOG | D:LOG | TOTAL | FLOW |
|---|---|---|---|---|---|---|
|  | —0 | —0 | —0 | —0 | —0 | "ENTER" |

The data fields of the display template are selectably resettable by pressing the reset key 146 in the appropriate data field.

An explain key 182 is provided on the front panel 124. The explain key 182 when pressed in sequence with any of the function keys described above provides an operator display template on the operator interactive display 126 that assists the operator in understanding the function of the corresponding key. Each key preferably should be held down within three seconds after the explain key is pressed to obtain an explanation of the key. Exemplary display templates are omitted for brevity of explication. A mute key 184 is provided on the front panel 124. The system controller is operative when the mute key 184 is pressed to silence the audible alarm.

A plurality of status LED's designated by a dashed box 186 are provided on the front panel 124. The status LED's 186 include an AC power LED 188, a battery LED 190, and an alarm LED 192. The AC power LED 188 provides a visual indication that the infusion system is operative under AC power, the battery LED 190 provides a visual indication that the infusion system is operative under internal battery power, and the alarm LED 186 provides a visual indication of either an alarm condition or an error condition. The system controller is operative to provide an alarm indication to indicate that infusion is complete on a line, to indicate that call back has been requested, to indicate an occlusion situation, to indicate air in line, to indicate a low battery condition, to indicate an out of place cassette, and to indicate that primary infusions are simultaneously scheduled. The system controller is operative to display the following display templates for each of the alarm conditions.

19. INFUSION COMPLETE START ANOTHER LINE OR STOP LINE—TO CLEAR ALARM

20. CALLBACK REQUESTED, START OR STOP LINES TO CLEAR ALARM

21. OCCLUSION IN PATIENT LINE CLEAR OCCLUSION & START LINES

22. AIR IN LINE OR UPSTREAM OCCLUSION PURGE AIR & START LINES

23. LOW BATTERY VOLTAGE CONDITION PLUG AC CORD INTO RECEPTICLE

24. CASSETTE LOCK LEVER NOT IN PLACE RETURN TO LOCK POSITION & START LINES

25. PRIMARY INFUSIONS OCCUR SIMULTANEOUSLY MUST RE-PROGRAM START TIME

The system controller is operative to provide an error indication to indicate pump failure and to indicate an out-of-range entry or invalid key. The corresponding error display templates preferably have the following formats.

26. PUMP FAILURE SERVICE REQUIRED

27. VALUE OUT OF RANGE OR INVALID KEY: PRESS RESET KEY FOR HOME OMNIGRAM: READ MANUAL

The system controller is operative to display the following "home" display template indicating system status whenever it does not display any of the above described display templates.

| 28. | A:OFF | B:OFF | C:OFF | D:OFF | TOTAL | 12:00 AM |
|---|---|---|---|---|---|---|
|  | 0 | 0 | 0 | 0 | 0 | ML/HR |

The states for each of the lines will be either "OFF", "PGM", "ON", "OVR", or "KVO". "OFF" indicates that the corresponding line is in an inactive state; "PGM" indicates that the corresponding line has been programmed to pump at a selected rate, volume, and time; "ON" indicates that the corresponding line is pumping; "OVR" indicates that the corresponding line is in the override state; and "KVO" indicates that the corresponding line is in a keep vein open mode.

Additional display templates to set current time, to select maximum occlusion pressure, to select maximum infusion rate, and to select a keep-vein-open mode and rate are displayed by pressing the "*" key 174 followed by a corresponding data key "1", "2", "3", and "4". These display templates preferably have the following format.

29. CURRENT TIME__:__"ENTER"

30. MAXIMUM OCCLUSION PRESSURE: __PSI "ENTER"

31. MAXIMUM TOTAL INFUSION RATE: __ML/HR "ENTER"

32. KVO RATE: __ML/HR "ENTER"

The operator then presses the "enter" key and the selected data is entered into the corresponding address locations provided therefor in the data file for each display template.

Figure 4A:
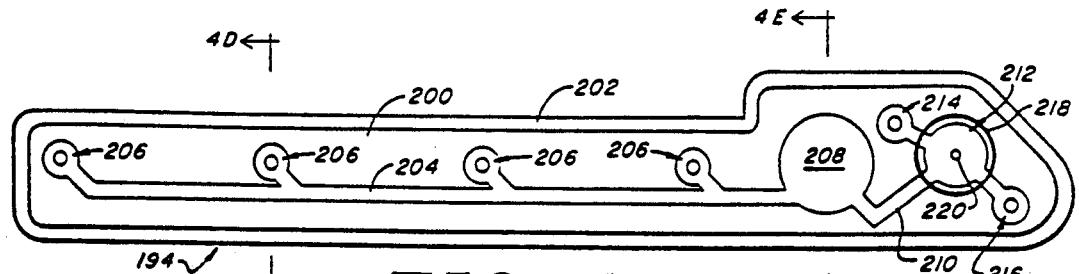
FIG. 4A is a plan view illustrating one portion of a cassette of the infusion system having plural fluid input ports and at least one patient output port according to the present invention.
Figure 4C:
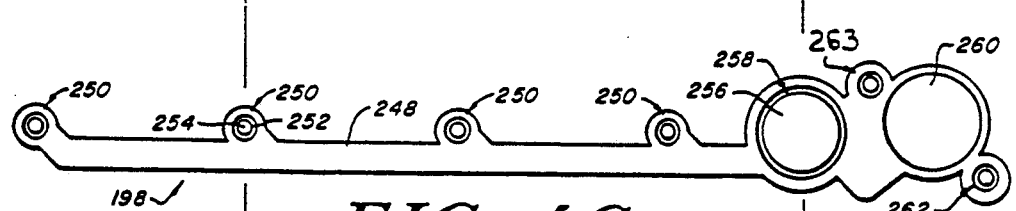
FIG. 4C is a plan view illustrating a flexible diaphragm of the cassette of the infusion system having plural fluid input ports and at least one patient output port according to the present invention.
Figure 4B:
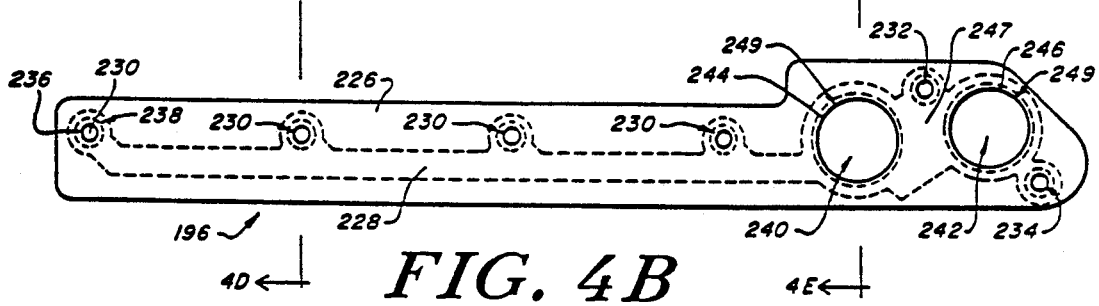
FIG. 4B is a plan view illustrating another portion of the cassette of the infusion system having plural fluid input ports and at least one patient output port according to the present invention.

Referring now to FIG. 4, generally illustrated at 194 in FIG. 4A is a first housing portion, generally designated at 196 in FIG. 4B is a second housing portion, and generally designated at 198 in FIG. 4C is a flexible diaphragm of a disposable cassette of the infusion system having plural fluid input ports and at least one patient output port according to the present invention. As shown in FIG. 4A, the housing portion 194 includes an injection molded clear plastic member 200 that meets appropriate U.S. Pharmacopia standards. The member 200 includes an integral upstanding peripheral flange 202 and a longitudinally extending fluid flow channel 204. A plurality of longitudinally spaced fluid input apertures generally designated 206 and a pumping chamber generally designated 208 are integrally formed with the member 200 in communication with the fluid flow path channel 204. A channel 210 is integrally formed with the plastic material 200 between the pumping chamber 208 and a pressure chamber generally designated 212. The chamber 212 is integrally formed with the plastic material 200. A patient output aperture generally designated 214 and a vent output aperture generally designated 216 are integrally formed with the plastic material 200 and are in fluid communication with the pressure chamber 212. A disc 218 having a central aperture 220 is provided over the pressure chamber 212 that cooperates with the walls defining the pressure chamber to prevent the collapse of the diaphragm 198 (FIG. 4C) into the chamber 212. As best seen in FIG. 4D, the cassette housing portion 194 includes an annulus 222 defining an input fluid port integrally formed surrounding a corresponding one of the fluid apertures 206, 214, 216 (FIG. 4A). Diametrically opposed locking flanges 224 are integrally formed on the ends of each annulus 222. The plastic member 200 includes longitudinally extending shoulders 225 that abut longitudinally extending guides provided therefor on the side of the housing 88 (FIG. 2A) that prevents the movement of the cassette 94 (FIG. 3A) in a direction transverse to its plane.

Referring now to FIG. 4B, the housing portion 196 includes a clear plastic member 226 that mates in fluid tight sealing engagement with the housing portion 194 (FIG. 4A). The member 226 includes a longitudinally extending diaphragm receiving recess 228. A plurality of longitudinally spaced input valve plunger receiving apertures generally designated 230 are provided through the plastic member 226. An output valve plunger receiving aperture 232 is provided in the plastic member 226 and a vent valve plunger receiving aperture 234 is provided in the plastic member 226. An upstanding annular flange 236 integrally formed with the plastic member 226 is provided surrounding each of the input valve plunger receiving apertures 230, the vent valve plunger receiving aperture 234, and the output valve plunger receiving aperture 232. A semicircular channel portion generally designated 238 integrally formed in the plastic member 226 is provided surrounding each of the annular flanges 236 that are in communication with the channel 228. The plastic member 226 of the housing portion 196 includes a pumping piston receiving aperture generally designated 240 and a pressure transducer receiving aperture generally designated 242. An annular flange 244 integrally formed in the plastic member 226 in communication with the channel 228 is provided surrounding the aperture 240, and an annular flange 246 integrally formed in the plastic member 226 is provided surrounding the aperture 242. Semicircular channel portions generally designated 249 are also provided around the annular flanges 244, 246. A recess 247 is provided intermediate the flanges 244, 246 forming a continuation of recess 228. The ends of the flanges 236, 244, 246 are flush with the generally planar surface of the plastic member 226.

Referring now to FIG. 4C, the diaphragm 198 is preferably an injection molded length of silicone rubber that meets the appropriate U.S. Pharmacopia standards. The diaphragm 198 includes a longitudinally extending reinforced seal portion 248 having a transverse width greater than the transverse width of the longitudinally extending fluid channel 204 (FIG. 4A) that is received in the recess 228 (FIG. 4B). A plurality of longitudinally spaced input fluid valve pads generally designated 250 are provided on the longitudinally extending reinforced seal portion 248. Individual ones of the valve pads 250 are aligned with corresponding ones of the apertures 206 (FIG. 4A) and apertures 230 (FIG. 4B). The valve pads 250 include an annular recess 252 that is individually aligned with a corresponding one of the annular flanges 236 (FIG. 2B) and an integral upstanding cylindrical projection 254 that are individually aligned with corresponding ones of the apertures 206 (FIG. 4A) and apertures 238 (FIG. 4B).

A convex dome 256 surrounded by an annular recess generally designated 258 is provided on the diaphragm 198. The recess 258 is aligned with the annular flange 244 (FIG. 4B) and the dome 256 is aligned with the aperture 240 (FIG. 4B) and the pumping chamber 208 (FIG. 4A). A thin circular portion 260 is provided on the diaphragm 198. The portion 260 is aligned with the flange 246 (FIG. 4B) and with the pressure chamber 218 (FIG. 4A). A vent valve pad generally designated 262 is provided on the diaphragm 198 between the members 256, 260 in alignment with the apertures 216 (FIG. 4A), 234 (FIG. 4B), and a patient output valve pad generally designated 263 is provided adjacent the cylindrical depression 258 in alignment with the apertures 214 (FIG. 4A), 232 (FIG. 4B). Each of the pads 262, 263 include an integral upstanding cylindrical projection surrounded by an annular recess like those described above for the pads 250. The cylindrical projections of the valve pads 250, 262, 263 have dimensions larger from the dimensions of the corresponding aligned apertures of the member 194 to provide a seal thereagainst to prevent fluid flow. The thickness of the portions 248, 256 (FIG. 4C) is selected to provide a stiffness sufficient to prevent their unintended collapse into the portions 204, 208 (FIG. 4A) during operation.

Figure 4D:
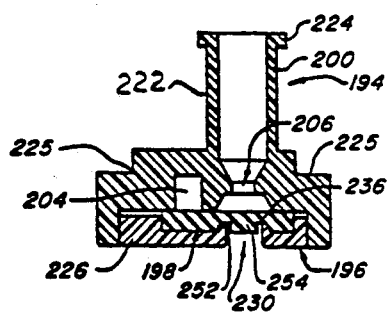
FIGS. 4D and 4E are sectional views of the cassette taken along the lines D—D and E—E of FIGS. 4A-4C of the infusion system having plural fluid inport ports and at least one patient output port according to the present invention.
Figure 4E:
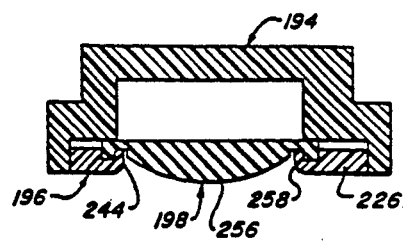

In the assembled condition of the disposable cassette as best seen in FIGS. 4D and 4E, the diaphragm 198 is sandwiched between the housing portion 194 and the housing portion 196. The longitudinally extending seal portion 248 of the diaphragm 198 is received in the diaphragm receiving recess 228, the solid cylindrical projections 254 of the valve pads 250, 262, 263 extend into corresponding ones of the apertures 230, 232, 234, the dome portion 256 is received over the mouth of the pumping chamber 208, and the cylindrical depression 254 is received over the disc 218 and pressure chamber 212. Any suitable means such as ultrasonic welding may be employed to secure the two housing portions together in fluid tight sealing engagement. The cassette is oriented in use preferably at 45° to the vertical as described above in connection with the description of FIG. 3A. As will readily be appreciated, any air in the fluid flow channel 204 (FIG. 4A) rises upwardly there-along through the pumping chamber 208 (FIG. 4A) and fluid path 210 into the pressure chamber 212 (FIG. 4A). As appears below, the system controller is operative to detect any air in the pressure chamber and to appropriately open the vent output valve to vent the air and to alarm should the condition persist. Since the air rises upwardly into the pressure chamber, the pumping chamber in normal operation is substantially free of air. When the pumping chamber is controllably exhausted, only the intended infusate is administered into the patient output port thereby preventing the possibility of admitting air into the patient.

Individual ones of a plurality of valve plungers to be described are received in corresponding ones of the apertures 230, 232, 234 (FIG. 4B) that are reciprocally moveable to push corresponding upstanding cylindrical projections 254 (FIG. 4D) into sealing contact with the apertures 206, 214, 216 to control the state of actuation of the corresponding fluid valves. The cylindrical projections with their associated plunger withdrawn flex out of contact with the corresponding apertures to allow fluid flow into and out of the pumping chamber 208. A pumping piston to be described is received in the pumping piston receiving aperture 240 (FIG. 4B). The piston is reciprocally moveable to controllably push the dome 256 (FIG. 4C) into the pumping chamber 208 as can best be seen in FIG. 4E. The fluid that accumulates therein during each pumping sequence to be described is thereby pumped through the patient output port and into the circulatory system of a patient. The rate of reciprocating motion of the pumping piston, its travel distance into the chamber 208, and the time interval between pumping strokes is selected to controllably administer intended volumes of infusant in intended time intervals.

Figure 5:
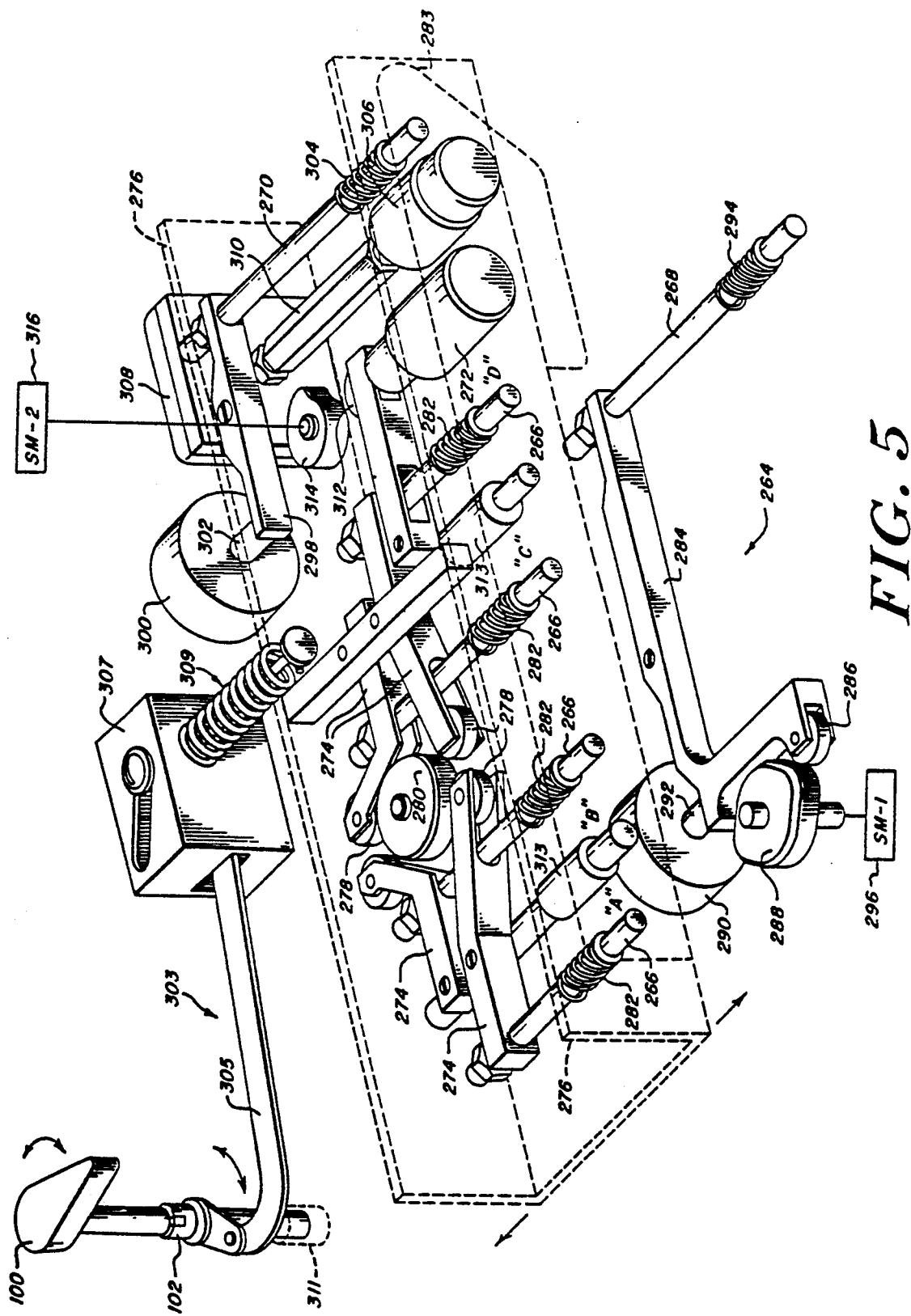
FIG. 5 is a partially exploded perspective view with the cover removed of a valve and pumping actuator of the infusion system having plural fluid input ports and at least one patient output port according to the present invention.

Referring now to FIG. 5, generally designated at 264 is a partially exploded perspective view with the cover removed of a valve and pumping actuator of the infusion system having plural fluid input ports and at least one patient output port according to the present invention. The assembly 264 includes a plurality of fluid input port valve plungers 266 each coaxially aligned with a corresponding one of the fluid input apertures 230 (FIG. 4D), an output valve port plunger 268 coaxially aligned with the output port aperture 232 (FIG. 4B), a vent valve port plunger 270 coaxially aligned with the collection bag aperture 234 (FIG. 4B), and a pumping chamber piston 272 coaxially aligned with the pumping chamber aperture 240 (FIG. 4E).

Each of the fluid input valve plungers 266 are slideably mounted in and fastened to a corresponding one of a plurality of rocker arms 274 that are individually pivotally mounted to a U-shaped support illustrated dashed at 276. A roller 278 is fastened to an end of each of the rocker arms 274. A cam 280 moving one lobe drives any selected one of the rollers 278 to withdraw the corresponding fluid input plunger 266 out of the corresponding ones of the fluid input port apertures. A compression spring 282 is slideably mounted on and fastened to corresponding ones of the plurality of fluid valve input plungers 266. The springs 282 act against one wall of the U-shaped support 276 urging the plungers 266 into corresponding ones of the fluid input ports designated "A", "B", "C", "D" of a cassette schematically illustrated at 283 to maintain the corresponding valves in a normally closed condition.

The output valve plunger 268 is slideably mounted in and fastened to one end a rocker arm 284 that is pivotally mounted to the support 276. A roller 286 is fastened to an end of the rocker arm 284 remote from the end in which the plunger 268 is mounted. A cam 288, having two lobes 180° apart, coaxial with the cam 280, drives the roller 286 to withdraw the output valve plunger 268 out of the output valve aperture. A solenoid 290 having a displacable ram 292 is fastened to the support 276 with its ram 292 in contact with the end of the rocker arm 284 remote from the plunger 268. The ram 292 is selectably actuable to withdraw the output valve plunger 268 out of the output valve aperture. A spring 294 is slideably mounted on and fastened to the plunger 268. The spring 294 acts against the one wall of the U-shaped support 276 urging the plunger 268 into the output port aperture for biasing the output valve in a normally closed condition. The cam 280 and the coaxial cam 288 are mounted for rotation with the shaft of a stepper motor 296. The system controller controllably rotates the stepper motor 296 to selectively actuate the input and output valves to implement a desired pumping sequence as appears more fully below. The lobes on the cams 280, 288 are so arranged as to prevent any input port and the output port from being simultaneously in an open condition for any rotary position of the stepper motor 296 to prevent unintended gravity flow infusion. Whenever it is desired to simultaneously open any input port and the output port such as during priming, the system controller rotates the stepper motor 296 to the position that opens the selected input port and actuates the solenoid 290 to open the output port.

The vent plunger 270 is slideably mounted in and fastened to a rocker arm 298 that is pivotally mounted to the U-shaped support 276. A solenoid 300 having a displaceable ram 302 is fastened to the support with its ram 302 in contact with the rocker arm 298. The ram 302 is selectably actuatable to withdraw the vent output valve plunger 270 out of the collection bag output aperture to open the vent valve. A spring 304 is slideably mounted on and fastened to the vent plunger 270. The spring 304 acts against one wall of the U-shaped support 276 urging the plunger 270 into the collection bag port to maintain the vent valve in a normally closed condition.

A pressure head 306 fastened to a pressure transducer 308 via a longitudinally adjustable mechanical linkage 310 is coaxially aligned with the pressure chamber. The pressure head 306 includes an internal coaxial rod, not shown, positioned over the aperture 220 (FIG. 4A) that is displaced in a direction along its length in response to pressure variations in the pressure chamber 212 (FIG. 4A). The pressure transducer 308 converts the linear movement into an analog signal proportional to pressure in the pressure chamber.

A roller 312 is fastened to the end of the pumping piston 276 that is remote from the end that enters the pumping chamber 208 (FIG. 4A). A cam 314 having a spiral shaped bearing surface mounted for rotation with the shaft of a stepper motor 316 selectively drives the roller 312 for controllably displacing the pumping piston 272 for reciprocating motion into and out of the pumping chamber 208 (FIG. 4A). The support 276 is mounted in the housing for sliding motion by a mechanical linkage generally designated 303 connected between the lever 100 and the support 276. The linkage 303 includes a rod 305 pivotally mounted on one end to the lever 100 and connected on its other end to a member 307. A spring biased rod generally designated 309 is connected on one end to the support 276 and on its other end to a cam, not shown, interiorly of the member 307. A microswitch 311 is provided for sensing the axial position of the lever 100. Lifting the lever 100 axially out of the safety mechanism 102 and rotating it either clockwise or counterclockwise displaces the member 307 thereby urging the rod 309 toward and away from the support 276 for moving the support 276 and therewith the plungers and pistons into and out of the associated apertures provided therefor on the cassette. The switch 311 senses the axial position of the lever 100 to provide an indication of whether or not the cassette is locked in place. Extending alignment rods 313 are provided that cooperate with associated apertures provided therefor on the cassette, not shown, to help align the cassette in its intended operating position.

Figure 6:
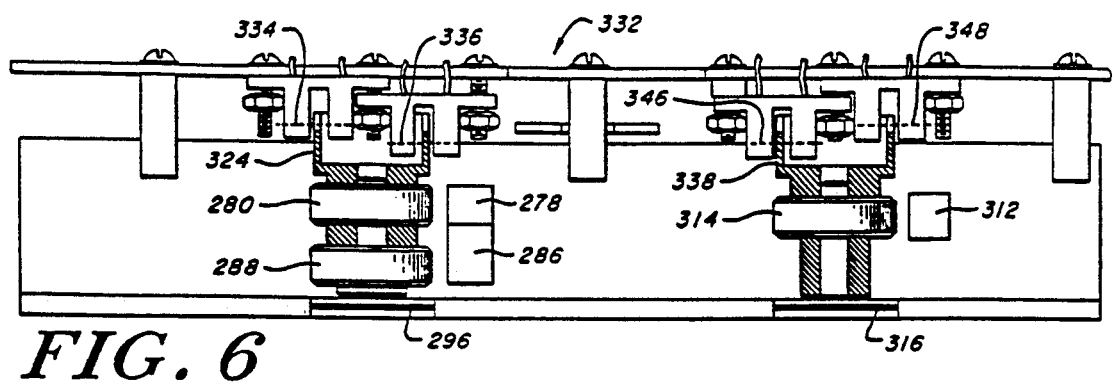
FIG. 6 is a side view of the valve and pumping actuator illustrating rotary position sensors of the infusion system having plural fluid input ports and at least one patient output port according to the present invention.
Figure 7:
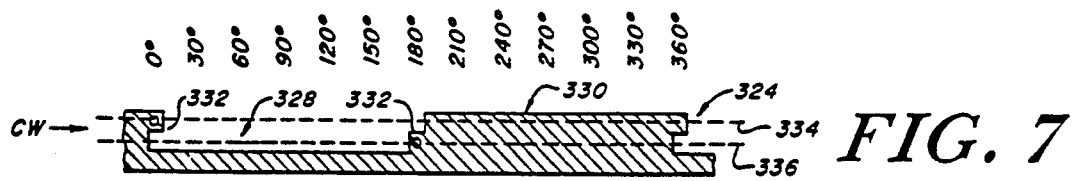
FIG. 7 is a rolled out view illustrating a position sensor for the valve actuator of the infusion system having plural fluid input ports and at least one patient output port according to the present invention.

Referring now to FIG. 6, generally designated at 332 is a side view of the valve and pumping actuator illustrating position sensors of the infusion system having plural fluid input ports and at least one patient output port according to the present invention. The position sensors are operative to provide signal indications of the intended rotary position of the stepper motors. An annular sleeve 324 is mounted for rotation with the cams 280, 288 and stepper motor 296. As best seen in rolled out view in FIG. 7, the annular sleeve 324 has an open portion generally designated 328 and a closed portion generally designated 330. As shown in FIGS. 6 and 7, a dashed line 334 designates a first light path and a dashed line 336 designated a second light path through which the sleeve 324 rotates. The light paths 334, 336 may be provided by any suitable light emitting and light receiving devices such as infrared emitters and cooperative infrared detectors. As the sleeve 324 rotates it alternately transmits and occludes the light paths 334, 336 providing signal indications to be described of the rotary position of the stepper motor 296 to insure its intended rotary position.

Figure 8:
FIG. 8 is a rolled out view illustrating a position sensor for the pumping actuator of the infusion system having plural fluid input ports and at least one patient output port according to the present invention.

An annular sleeve 338 is mounted for rotation with the cam 314 and the stepper motor 316. As best seen in rolled out view in FIG. 8, the sleeve 338 has an open portion generally designated 342 and a closed portion generally designated 344. As shown in FIGS. 6 and 7, a dashed line 346 designates a first light path and a dashed line 348 designates a second light path through which the sleeve 338 rotates. As the sleeve 338 rotates it alternately occludes and transmits the light paths 346, 348 providing signal indications to be described of the rotary position of the stepper motor 316 to insure its intended rotary position.

Figure 9:
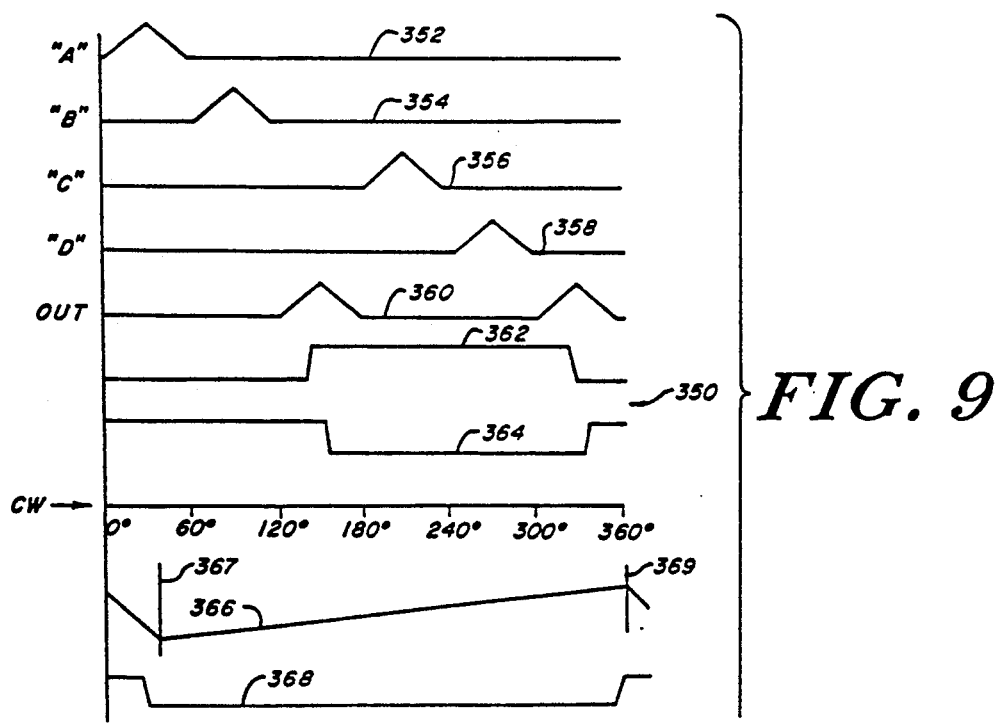
FIG. 9 is a rolled out view illustrating the operation of the valve and pumping actuator and position sensors of the infusion system having plural fluid input ports and at least one patient output port according to the present invention.

Referring now to FIG. 9, generally designated at 350 is a rolled out diagram illustrating the operation of the valve and pumping actuator and position sensors of the infusion system having plural fluid input ports and at least one patient output port according to the present invention. A line 352 illustrates the state of actuation of the "A" fluid input port (FIG. 1), a line 354 illustrates the state of actuation of the "B" fluid input port (FIG. 1), a line 356 illustrates the state of actuation of the "C" fluid input port (FIG. 1), and a line 358 illustrates the state of actuation of the "D" fluid input port (FIG. 1). The states of actuation 352, 354, 356, 358 depend on the rotary position of the stepper motor 296 (FIG. 5) that drives the cam 280 (FIG. 5) into contact with selected ones of the rollers 278 (FIG. 5) thereby displacing the corresponding plungers 266 (FIG. 5) out of contact with the corresponding cylindrical valve projection 254 (FIG. 4D). A line 360 illustrates the state of actuation of the patient output port 26 (FIG. 1). The state of actuation of the output port depends on the rotary position of the stepper motor 296 (FIG. 5) that drives the cam 288 into contact with the roller 286 (FIG. 5) thereby displacing the plunger 268 out of contact with the cylindrical valve projection 254 (FIG. 4D). When any one of the fluid input port valves are in an open condition as illustrated by the "peaked" portions of the lines 352, 354, 356, 358, fluid from the corresponding fluid container flows into the disposable cassette 94 (FIG. 3A) along the longitudinally extending fluid flow channel 204 (FIG. 4A) and into the pumping chamber 208 (FIG. 4A) so long as the corresponding fluid input port is maintained in an open condition and the pumping piston is withdrawn out of the pumping chamber. After filling the pumping chamber with the selected fluid from any one of the plural fluid input ports, the system controller is operative to rotate the cam 288 (FIG. 5) to either of the two "peaked" positions of the line 360 (FIG. 9) to open the output valve 26 (FIG. 1) to allow fluid to flow through the patient line 120 (FIG. 3A). The system controller during a pumping sequence is operative to take several pressure measurements and to alarm when appropriate in a manner to be described. Fluid admitted into the cassette from the "B" and from the "C" fluid input ports are administered from the left hand "peaked" position of the line 360, and fluid admitted into the cassette from either the "A" and from the "D" fluid input ports are administered from the right hand "peaked" position of the line 360. In priming mode for the patient output line, the system controller is operative to rotate the stepper motor 296 to the position that opens the selected one of the fluid input ports, and to activate the solenoid 290 (FIG. 5) to open the patient output valve to allow priming fluid to flow from the selected fluid input port through the cassette and into the patient output line to prevent the possibility of admitting air into the patient. The sleeve 326 (FIG. 6) alternately occludes and transmits light along the light paths 334, 336 (FIG. 6) producing signal indications designated 362 and 364 of the rotary position of the stepper motor 296 (FIG. 6) to within one step accuracy of the left and right hand "peaked" positions of the line 360. As appears below, the signals 362 and 364 are used by the system controller to insure the proper orientation of the cam 280 (FIG. 5). A line 366 illustrates a pumping sequence of the pumping plunger 272 (FIG. 5), beginning at a vertical line designated 367 and ending at a vertical line designated 369. The sleeve 338 (FIG. 6) alternately occludes and transmits light along the light paths 346, 348 (FIG. 6) producing signal indications 368, 370 of the position of the stepper motor 316 (FIG. 6) to within one step accuracy of the start and end positions of the piston 242 (FIG. 5) during a pumping sequence. As appears below, the signals 368, 370 are used by the system controller to insure proper orientation of the cam 314 (FIG. 5).

Figure 10:
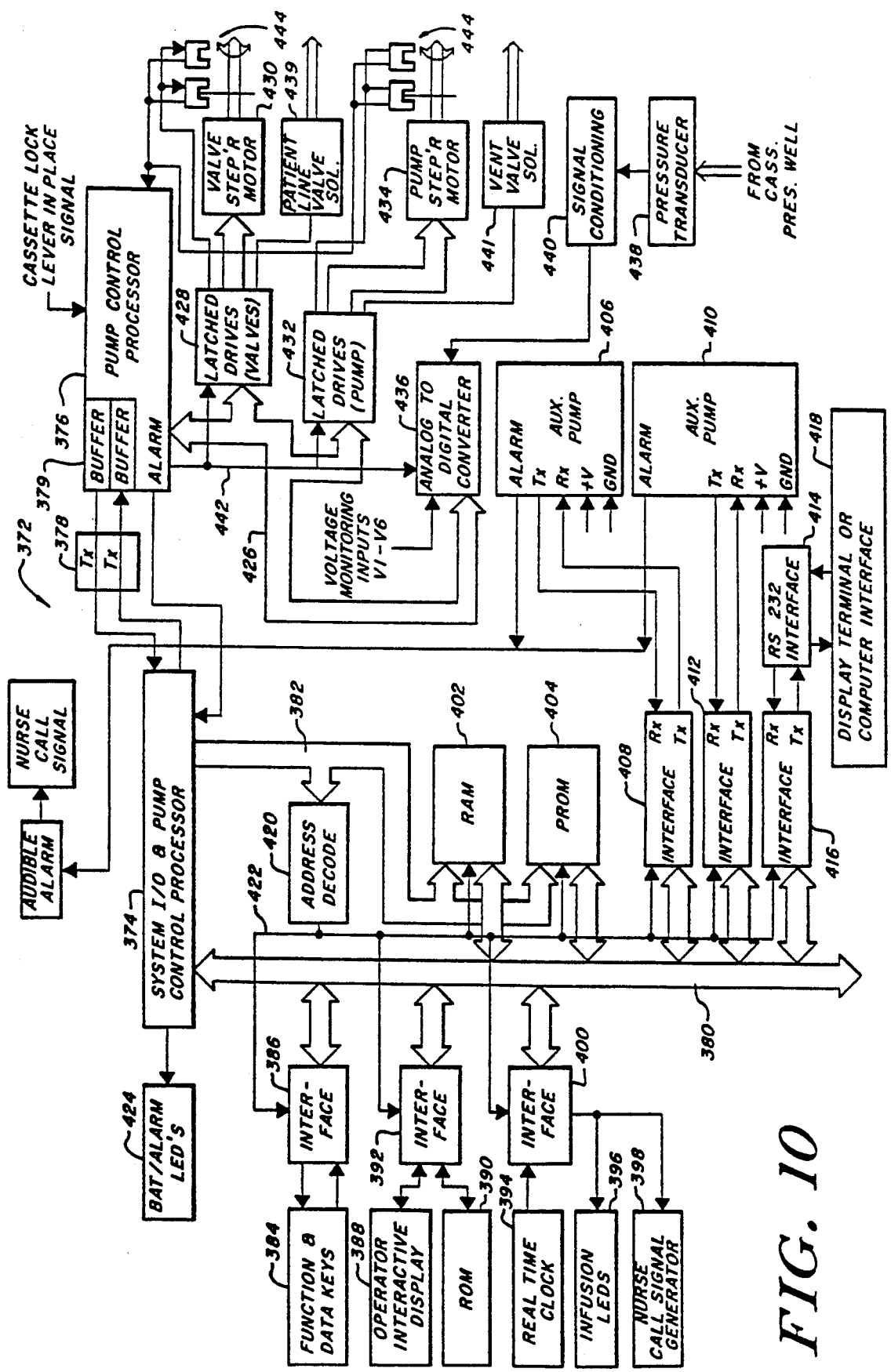
FIG. 10 is a schematic diagram of the system controller of the infusion system having plural fluid input ports and at least one patient output port according to the present invention.

Referring now to FIG. 10, generally designated at 372 is a schematic diagram illustrating a preferred embodiment of the system controller of the infusion system having plural fluid input ports and at least one patient output port according to the present invention. The system controller 372 includes a first processor 374 and a second processor 376 slaved to the first processor 374. A bit serial asynchronous communication link 378 interconnects the processors 374, 376. The processor 374 controls operator input and output (I/O), and down loads instructions over the serial communication link 378 into dual ping-pong buffers 379 for execution by the processor 376. The processor 376 controls in accordance with the instructions the state of actuation of the fluid input port valves and of the patient and vent output valves, controls the reciprocating motion of the pumping chamber piston at a rate and for a duration specified by the instructions, reads information representative of the pressure in the pressure chamber and writes information to the processor 374 representative of alarm situations and pressure data. As appears more fully below, the processor 374 is operative in response to the measured pressure data to adjust the reciprocating motion of the pumping piston to adapt desired to actual fluid flow rates.

The system I/O and pump control processor 374 includes a data bus 380 and an address bus 382 connected thereto in the usual manner. A plurality of function and data keys 384 described above in connection with the description of FIG. 3B are connected by an interface 386 to the data bus 380. An operator interactive display 388 described above in connection with the description of FIG. 3B and an associated electrically erasable E2 ROM 390 are connected to the data bus 380 by an interface 392. A real time clock 394, a plurality of infusion LED's 396, and a nurse call signal generator 398 are connected by an interface 400 to the data bus 380. A data RAM 402 is connected to the data bus 380 and to the address bus 382. A program PROM 404 is connected to the address bus 382 and to the data bus 380. An auxiliary pump processor 406 is connected to the data bus 380 via an interface 408 and a second auxiliary pump 410 is connected to the data bus 380 via an interface 412. A RS 232 interface 414 is connected to the data bus 380 via an interface 416. A peripheral device 418 such as a display terminal or a central control computer interface is connected to the RS 232 interface 414. The interfaces 386, 392, 400, 408, 412, and 416 format and buffer data between the data bus and the associated devices in a manner well known to those skilled in the art. An address decoder 420 is connected to the address bus and to the interfaces 382, 392, 400, 408, 412, and 416 via a plurality of control lines 422. The address decoder 420 decodes the addresses appearing on the address bus and activates the corresponding control line to enable the addressed peripheral device for data reads and writes via the data bus 380. Battery and alarm LED's 424 described above in connection with the description of FIG. 3B are operatively connected to the processor 374.

Referring now to FIG. 11, generally designated at 426 is a data file of the RAM 402 (FIG. 10). The data file 426 includes a block of selectively addressable RAM memory generally designated 428 for fluid input port "A", a block of RAM memory generally designated 430 for fluid input port "B", a block of RAM memory generally designated 432 for fluid input port "C", and a block of RAM memory generally designated 434 for fluid input port "D". Each block of RAM memory 426, 428, 430, and 432 at corresponding preselected address locations thereof specify an operator selected data structure for the corresponding fluid input port. The system I/O and pump control processor 374 selectively addresses the RAM 402 (FIG. 10) over the address bus 382, and writes into the selectively addressed RAM location the data selected by the operator over the data bus 380 as described above in connection with the description of FIG. 3B. The data structure for each line includes data representative of whether it is a primary or piggyback line. The data structure for primary lines includes data representative of infusion rate, infusion volume, infusion duration, and fluid container volume. The data structure for piggyback lines includes data representative of dilute line, dilute volume, and dilute rate for piggyback dilutions, and data representative of duration (Q) and repeat interval (X) for time sequential piggyback lines. The data structure for each line includes data representative of "prime" mode, "override" mode, and "normal-on" mode, and data representative of start time either after a selected delay or after infusion on a designated line. The data structure for each line includes data representative of syringe, and the preselected line for unsticking the syringe plunger. The data structure for each line includes data representative of flush and the selected flush line, flush volume, and flush rate. The data structure for each line further includes data representative of "call back", and data representative of measured pressure including patient pressure, compliance pressure, and bottlehead pressure to be described.

The data file 426 includes a block of selectably addressable RAM memory generally designated 436. The data structure of the block of RAM 436 for each line specifies data representative of the current history of the infusions already pumped on that line.

The data file 426 includes a block of selectively addressable RAM memory generally designated 438 that specify global parameters for all the lines. The data structure of the block of RAM 438 specifies data representative of current time, maximum occlusion pressure, maximum infusion rate and volume, and KVO rate.

Returning now to FIG. 10, the PROM 404 includes in preselected address locations thereof the code specifying the program for the system I/O and pump control processor 374. The PROM 404 also includes at preselected address locations thereof the display templates that prompt the system operator for both selecting a desired course of infusion and for selecting and controlling system operation described above in connection with the description of FIG. 3B.

A data bus 426 is operatively connected to the pump control processor 376. RAM and PROM for the pump processor, not shown, are associated therewith in the usual manner. The pump control processor PROM contains the code specifying any one of possible pumping sequences to be described. Conventional latched drives 428 operatively connected to the data bus 426 are connected to a valve stepper motor 430. Conventional latched drives 432 operatively connected to the data bus 426 are connected to a pump stepper motor 434. An analog to digital converter (ADC) 436 operatively connected to the data bus 426 is connected to a pressure transducer 438 via a conventional analog signal conditioning module 440. Voltage inputs designated "$V_1$-$V_6$" are connected to the ADC 436 to monitor system power level as described above in connection with the description of FIG. 1. A plurality of control lines 422 are operatively connected to the pump control processor 376 for selecting the latched drives 428, for selecting the latched drives 432, and for selecting the analog to digital converter 436. A patient line solenoid 439 is connected to the latched drives 428, and a vent valve solenoid 441 is connected to the latched drives 432. Position sensors generally designated 444 operatively connected to the pump control processor 376 and the latched drives 428, 432 provide signal indications representative of the rotary position of the valve stepper motor 430 and of the rotary position of the pump stepper motor 434 described above in connection with the description of FIGS. 6-9. The pump control processor is operative in the usual manner to enable selected ones of the devices 428, 432, and 436 by the corresponding control line, and to read and write at the appropriate times during a pumping sequence data thereto over the data bus 426.

Referring now to FIG. 12, generally designated at 448 is a table illustrating an instruction byte produced by the system I/O and pump control processor 374 (FIG. 10) for controlling the pump control processor 376 (FIG. 10). The instruction byte includes eight bits designated 0 through 7. The one bit designated "ALL" of the bit field specifies that all data read by the pump processor is to be read by to the system I/O and pump control processor. The two bit designated "$V_1$-$V_6$" of the bit field specifies that the battery and regulator voltage data measured by the analog to digital converter is to be read by the system I/O and pump control processor. The three bit of the bit field designated "$D_0$-$D_7$ and $C_4$" specifies either that the maximum occlusion pressure are to be written by the system I/O and pump processor to the pump processor or that the pressure and error data bytes "$D_0$-$D_7$" to be described are to be read by the system I/O and pump control processor from the pump processor. The four bit designated "norm and other" of the bit field specifies whether the system is to operate in the normal mode or not. The five bit designated "read/write" of the bit field specifies whether data is to be read by the pump control processor or whether data is to be written by the pump control processor. The six bit designated "X/Y" of the bit field specifies which of the ping-pong buffers is to be receive the next command. The seven bit designated "abort" of the bit field specifies whether an abort is to be effected by the pump control processor. As shown by the table 448, the first instruction specifies whether the X or the Y buffer is to be aborted. The second instruction reads a status byte designated "S" to be described. The third instruction reads $D_0$ through $D_7$. The fourth instruction reads $V_0$ to $V_6$. The fifth instruction reads S, $D_0$ through $D_7$, $V_0$ through $V_6$, and $C_0$ through $C_4$ to be described. The sixth instruction writes $C_0$ through $C_3$ and reads $D_0$ through $D_2$. The seventh instruction writes $C_4$, and reads $D_3$. The eighth instruction instructs the pump processor to take a reference pressure measurement designated 0 PSI to be described.

Referring now to FIG. 13A, generally designated at 450 is a status byte "S". The status byte is produced by the pump control processor and includes data representative of the state of the X, Y ping-pong buffers and of the mode of operation of the pump control processor. The status byte 450 includes eight bit positions 0 through 7, with the zero and one bits of the bit field specifying control mode, the second bit of the bit field specifying Y error buffer, the third and fourth bits of the bit field specifying the state of Y buffer, the fifth bit of the bit field specifying an X buffer error, and the sixth and seventh bits of the bit field specifying the state of the X buffer. As shown in the state table, a "0, 1" specifies that the corresponding X or Y buffer is waiting to execute; a "1, 0" specifies that the corresponding instruction is being executed; a "1, 1" specifies that the corresponding buffer is ready for a new instruction; and a "0, 0" specifies an initialization state for the corresponding buffer. As shown in the control table designated "CNTL", a "0, 0" specifies continuing the current control function and a "1, 1" specifies stopping the current function.

Referring now to FIG. 13B, generally designated at 452 in a timing diagram illustrating the communications protocol of the processors 374, 376 (FIG. 10). The boxes above the dashed line 454 illustrate the instructions written from the system I/O and pump control processor 374 to the pump control processor 376, and the boxes below the dashed line 454 illustrate the data read from the pump control processor by the system I/O and pump control processor 374. For the exemplary communications protocol, the pump control processor 374 sends over the transmission link 378 an instruction designated "I RD STAT" to read the status byte as illustrated at 456. The pump control processor 376 receives the instruction as illustrated at 458, and sends the status byte having the control bits "0, 0" back to the system I/O and pump control processor 374 as illustrated at 460. The system I/O and pump control processor receives the status byte as illustrated at 462, and sends it back to the pump control processor instructing it to continue as illustrated at 464. The process continues until the system I/O and pump control processor 374 instructs the pump control processor 376 to stop as illustrated by the box 466 having the control bits "1, 1". The pump control processor continues until it receives the instruction to stop as illustrated at 468 and sends it back to the system I/O and pump controller processor as illustrated by the box 470. The system I/O and pump control processor then sends an acknowledge instruction designated "ACK" to the pump control processor as illustrated by the box 472, which is received by the pump control processor 376 as illustrated by the box 474. It will be appreciated that a similar communications protocol is implemented for each of the instructions and commands written by the system I/O and pump control processor to the pump control processor.

Referring now to FIG. 14, generally designated at 476 is the $C_0$ command byte; generally designated at 478 is the $C_1$ command byte, generally designated at 480 is the $C_2$ command byte, generally designated at 482 is the $C_3$ command byte, and generally designated at 484 is the $C_4$ command byte. The 0 through 6 bits of the bit field of the $C_0$ byte 476 specify a number of microstrokes per pump stroke, and the seventh bit of the bit field specifies priming. The 0 through 12 bits of the bit field of the $C_1$, $C_2$ bytes 478, 480 specify the time per pump stroke, preferably in tenths of a second, and the 13 through 15 bits of the bit field of the $C_1$ byte 478 designated "$T_0$-$T_2$" specify which of the pump processor PROM pumping sequences to be described is to be executed. The 0 through 4 bits of the bit field of the $C_3$ byte 482 specify the number of pump strokes, the fifth and sixth bits of the bit field of the $C_3$ byte 482 specify from which fluid input port fluid is to be administered, and the seventh bit of the bit field specifies either that the vent output valve or the patient line output valve are to be actuated. The $C_4$ byte 484 specifies the maximum occlusion pressure selected by the system operator.

Referring now to FIG. 15, generally designated at 488 is the $D_0$ data byte. The $D_0$ data byte represents the bottle height pressure designated "P2" read by the pump processor and written in pump processor RAM during the pumping sequence. The bottle height pressure is the ADC reading of the pressure chamber when only an input valve is open normalized by the 0 PSI value. The $D_1$ data byte is generally designated at 490.

The $D_1$ data byte represents the air-in-line compliance pressure designated "P4" read by the pump processor and written in pump processor RAM during the pumping sequence. The air-in-line compliance pressure as appears below is the difference of the ADC reading of the pressure chamber when the piston is successively driven partially in the pumping chamber and all valves are closed. The $D_2$ byte is generally designated at 492. The $D_2$ data byte represents volume correction designated "N1" and "N2" to be described read by the pump processor and written in pump processor RAM during the pumping sequence. The volume correction data as appears below depends on the pressure data and is employed to adapt actual to desired pumping rates. The $D_3$ data byte is generally designated at 494. The $D_3$ data byte represents the zero PSI pressure designated "P1" read by the pump processor and written in pump processor RAM during the pumping sequence. The 0 PSI pressure is the ADC reading of the pressure chamber when any input is just opened and the output valve is closed and the pumping piston is withdrawn prior to water hammer effects. The $D_4$ data byte is generally designated at 496. The $D_4$ data byte represents matching pressure designated "P3" to be described read by the pump processor and written in pump processor RAM during the pumping sequence. The $D_5$ data byte is generally designated at 498. The $D_5$ data byte represents the patient pressure designated "P5" read by the pump processor and written in pump processor RAM during the pumping sequence. The $D_6$ and $D_7$ bytes generally designated 500 and 502 have data therein representative of various error and alarm conditions that the pump controller monitors. The $D_6$ and $D_7$ data bytes are written during a pumping sequence in pump processor RAM. The $D_6$ and $D_7$ data bytes include data representing whether the stepper motors out are of proper rotary position, patient pressure greater than maximum occlusion pressure, air-in-line pressure less than minimum compliance pressure, empty bottle pressure, and cassette locking lever out of place.

Figure 16:
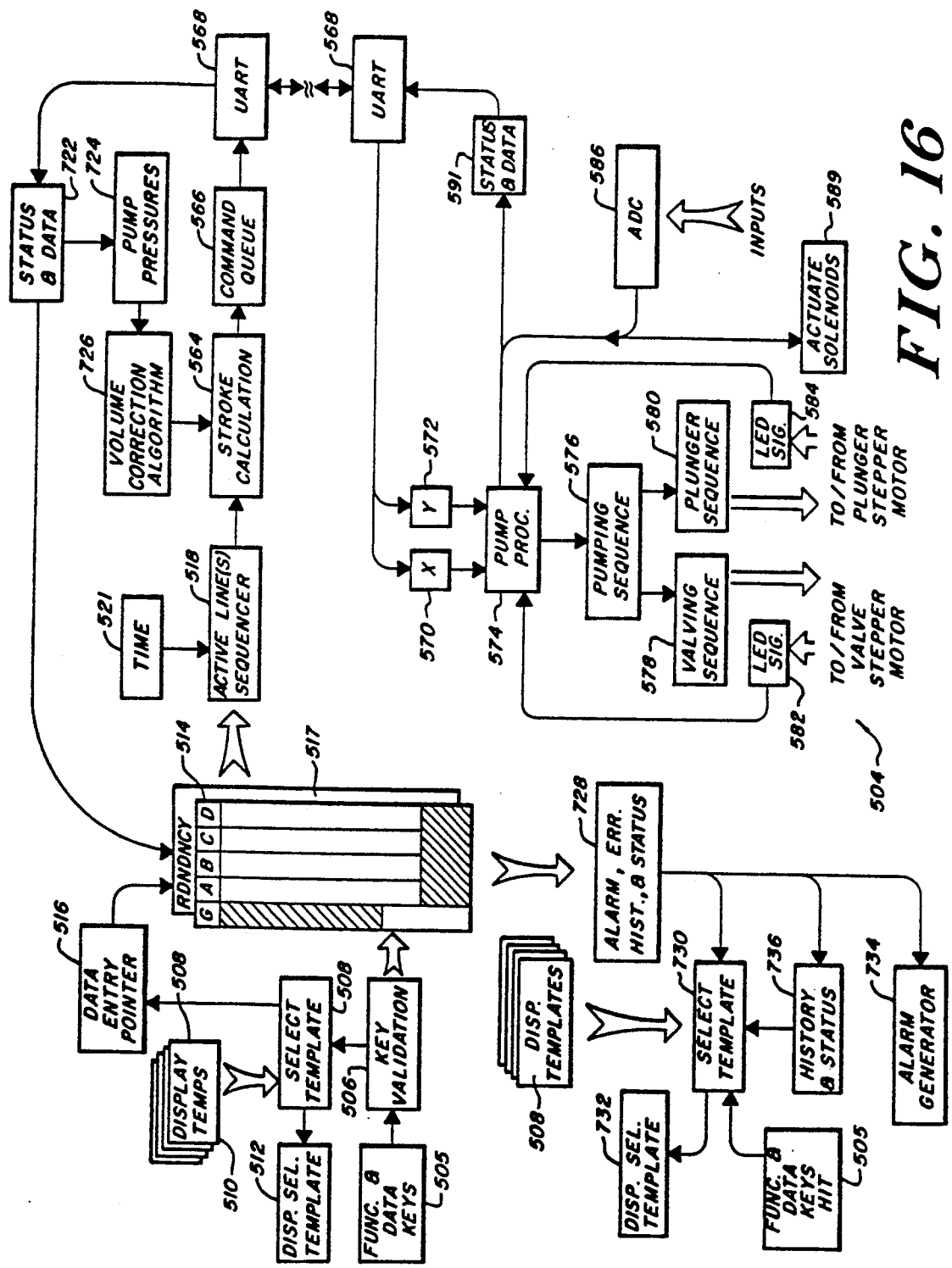
FIG. 16 is a data flow chart illustrating the operation of the infusion system having plural patient input ports and at least one patient output port according to the present invention.

Referring now to FIG. 16, generally designated at 504 is a data flow chart illustrating the operation of the infusion system having plural fluid input ports and at least one patient output port according to the present invention. As illustrated by the blocks 505, 506, the system I/O and pump control processor is operative to determine that a valid key, or combination of keys, has been entered. If a valid key or key combination has been entered, the processor is operative as shown by a block 508 to select the corresponding display template stored in PROM as shown by blocks 508, 510 and to display the selected template on the operator interactive display as shown by a block 512. If the display template corresponds to either the pump command display templates or the rate/vol/time display templates, the processor is operative to address for each data field the corresponding data locations in the data file 514 as illustrated by a block 516, and to write the operator selected data into the corresponding address locations of the data file for any selected one or more of the plural fluid input ports A, B, C, and D. As illustrated by a block 517, the system I/O and pump control processor is operative to write the data into the RAM data file to provide RAM redundancy for preventing errors. The 0 through 6 bits of the bit field of the $C_0$ command (FIG. 14) and the 13 through 15 bits of the bit field of the $C_1$ command (FIG. 14) are specified by the data file.

Figure 17:
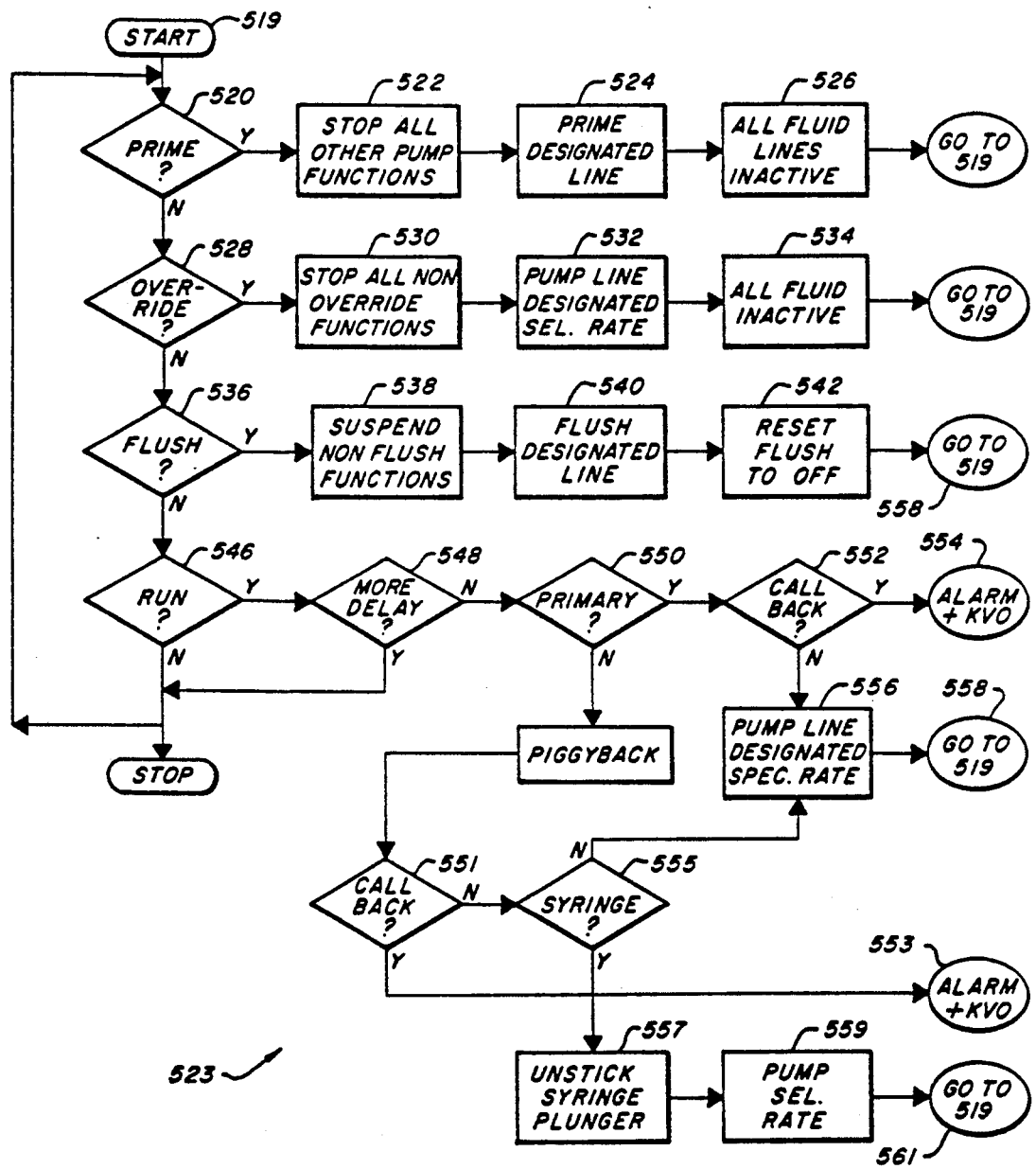
FIG. 17 is a flow chart illustrating the operation of the main control processor of the infusion system having plural fluid input ports and at least one patient output port according to the present invention.

As shown by a block 518 the system I/O and pump control processor is operative to read the data file address locations and the time as shown by a block 521 to determine if it should institute a pumping sequence on an active line. As shown in FIG. 17, which generally designates at 523 a flow chart of the active line sequencer, the processor is operative to determine whether the data file specifies operation in the priming mode as shown by a block 520. If the data file contains data representative of priming for any one of the input valves, the processor is operative to produce instructions to stop all other pump functions as shown by the block 522, to produce instructions to prime the designated line as shown by a block 524, to produce instructions to inactivate all the fluid lines as shown by a block 526, and to return processing to the block 519. If the data file specifies operation in the override mode as shown by a block 528, the processor is operative to produce instructions to stop all nonoverride functions as shown by a block 530, to produce instructions to pump the line designated at the specified rate as shown by a block 532, to inactive all fluid lines as shown by a block 534, and to return processing to the block 519. If the data file specifies operation in the flush mode as shown by a block 536, the processor is operative to produce instructions to suspend all nonflush functions as shown by a block 538, to produce instructions to flush the designated line as shown by a line 540, to reset the flush line as shown by a block 542, and to return processing to the block 519 as shown by a block 544. If the data file specifies operation in the auto-on mode as shown by a block 546, the processor is operative to determine whether the time for infusion is the present time or whether more delay is needed as shown by a block 548. If no more time is needed, the processor is operative to determine whether the data file designates the line as a primary line as shown by a block 550. If the line is a primary line, the processor is operative to determine whether the data file specifies call back as shown by a block 552. If call back is specified, the processor is operative to sound an alarm and to pump in the KVO mode as shown by a block 554. If no call back is specified in the data file, the processor is operative to produce instructions to pump the specified line as shown by a block 556, and returns processing to the block 519 as shown by a block 558. If the line is a piggyback line, the processor is operative as shown by a block 551 to determine whether call back is specified in the data file. If call back is specified in the data file, the processor is operative to sound an alarm and to pump in the KVO mode as shown by a block 553. If no call back is specified, the processor is operative to determine if the data file specifies a syringe as shown by a block 555. If a syringe is specified, the processor is operative to produce instructions to stop all other functions and to unstick the syringe plunger as shown by a block 557. The processor is then operative to produce instructions to pump from the syringe at the selected rate as shown by a block 559, and to return processing to the block 519 as shown by a block 561. If syringe is not specified, the processor is operative to produce instructions to pump the designated line at the specified rate as shown by the block 556, and returns processing to the block 519 as shown by the block 558. The active line sequencer specifies the 7 bit of the bit field of the $C_0$ command and the 5, 6, and 7 bits of the bit field of the $C_3$ command.

Returning now to FIG. 16, if any of the lines are active as described above in connection with the description of FIG. 17, the processor is operative to calculate the number of strokes for the pumping plunger to effectuate the desired duration and rate of infusion. The processor is preferably operative to calculate the number of strokes per second according to the following relation:

$$\frac{sec}{stroke} = \frac{Vol_{eff} * 3600}{RATE_I}$$

where $Rate_I$ is the specified infusion rate in milliliters per hour and $VOL_{eff}$ is the effective infused volume calculated as described below. The tenths of second per stroke data is written in the 0 through 12 bits of the bit field of the $C_1$ and $C_2$ commands bytes.

The processor is operative to buffer the instructions and commands described above in connection with the description of FIGS. 12 and 14 in a command queue as shown by a block 566, which are written to the pump control processor as shown by a block 568 into a specified one of the X or Y buffers as illustrated by the blocks 570, 572. As illustrated by a block 574, the pump control processor is operative to fetch the instructions from the appropriate buffer, and executes the specified pump control sequence as shown by a block 576 to controllably rotate the valve stepper motor to close and open the designated fluid input ports as illustrated by a block 578 and to controllably rotate the piston stepper motor to repetitively actuate the pumping piston as illustrated by a block 580. The pump control processor is operative during the pumping sequence to store in RAM the LED sensor signals from the valve stepper motor sleeve as illustrated by a block 582, and to store in RAM the LED sensor signals from the pump stepper motor sleeve as illustrated by a block 584. The pump processor is operative to read the analog to digital converter as shown by a block 586, to activate the vent output valve solenoid and the patient output line solenoid as shown by a block 589, and to write into pump control processor RAM the $D_0$–$D_7$ data as shown by a block 591 during the pumping sequence.

Figure 18:
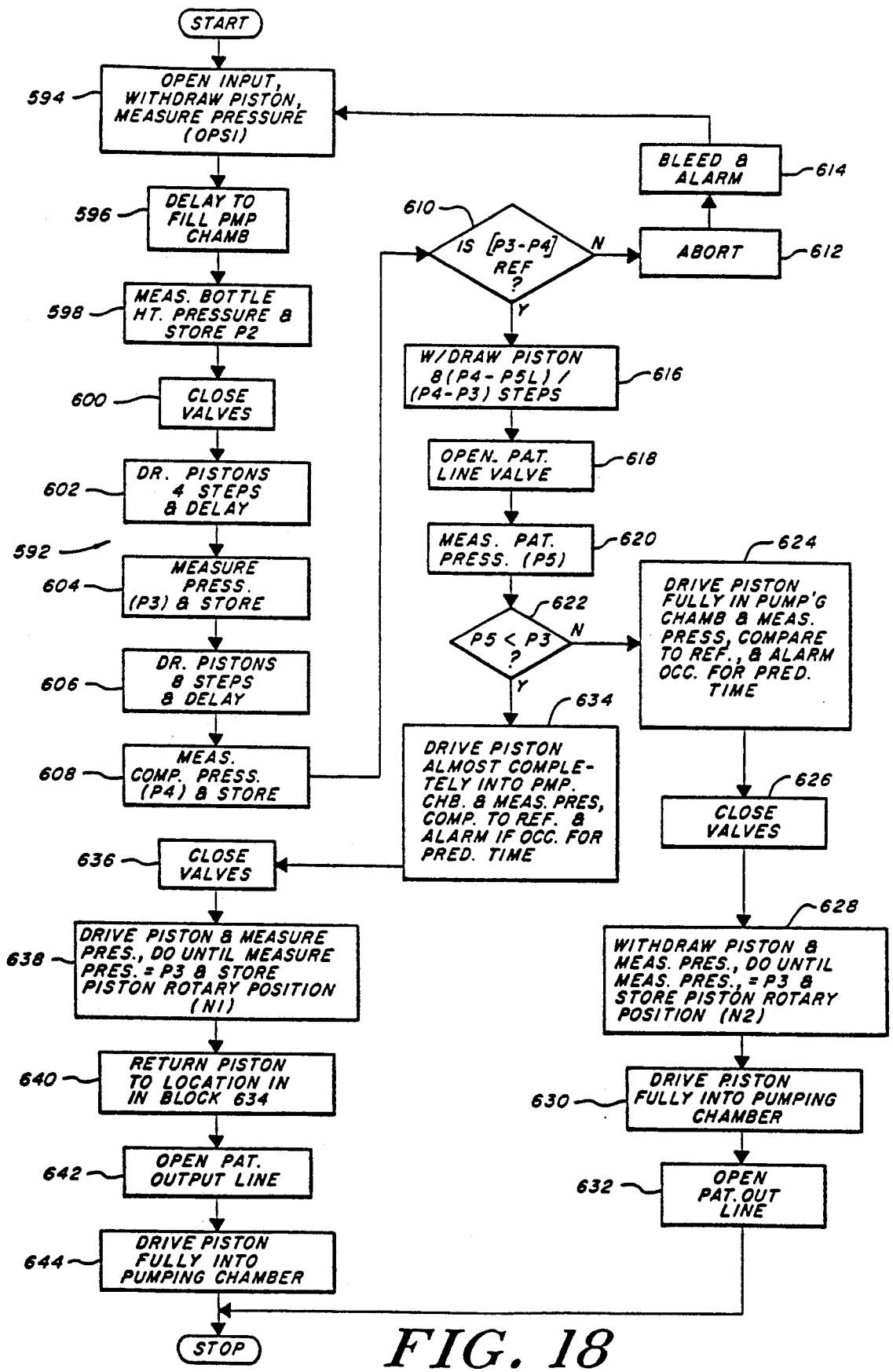
FIG. 18 is a flow chart illustrating one pumping sequence of the pump control processor of the infusion system having plural fluid input ports and at least one patient output port according to the present invention.

Referring now to FIG. 18, generally designated at 592 is a flow chart illustrating an exemplary pumping sequence of the pump control processor. The sequence 592 is preferably employed to controllably pump infusate at comparatively low operator selected rates of flow. As shown by a block 594, the processor is operative to open the specified one of the fluid input port valves, to withdraw the pumping piston, and to write the A/D reading into the $D_3$ RAM data location to measure 0 PSI. The processor is then operative to wait a predetermined time to allow fluid to flow from the selected input port into the pumping chamber as shown by a block 596.

The processor is then operative to write the A/D reading normalized by the 0 PSI reading into the $D_0$ data RAM location to measure the bottlehead pressure of the corresponding fluid container designated P2. The processor is then operative to close the valves as shown by a block 600 and to drive the pumping piston a selected distance, preferably four steps of the stepper motor, into the pumping chamber, and delays as shown by a block 602. The processor is then operative to write the A/D reading of the pressure transducer in RAM to take the matching pressure designated P3 as shown by a block 604. The processor is then operative to drive the pumping piston into the pumping chamber a further selected distance, preferably eight additional steps of the stepper motor, and delays as shown by a block 606. The processor is then operative to write the A/D reading of the pressure transducer designated P4 into RAM as shown by a block 608.

As shown by a block 610, the processor is then operative to compare the difference of the readings to determine whether air is in the line, to write the difference in the readings into the $D_1$ RAM data location, and to either proceed or alarm in dependence on whether the change in pressure is below a minimum preselected reference compliance pressure. As shown by a block 612, if air is in the line, the processor is operative to abort the pumping sequence. The processor is then operative to vent air from the line using a pumping sequence to be described, to alarm as shown by a block 614 if air is in the line preferably for three consecutive measurements, and processing for each measurement is returned to the block 594. As shown by a block 616, if no air is in the line, the processor is operative to withdraw the pumping piston out of the pumping chamber a preselected distance selected according to the measured pressures preferably calculated according to the relation 8(P4−P5L)/(P4−P3) steps of the stepper motor. The pressure P5L is the P5 pressure from the last stroke to be described. If P5L has yet to be measured in the pumping sequence, the processor assumes a specified value for the pressure P5L preferably equal to 0 PSI+5. The processor is then operative to open the patient output line valve as shown by a block 618 and to write the A/D reading of the pressure transducer into RAM to measure the patient pressure designated P5 as shown by a block 620.

As shown by a block 622, the processor is then operative to determine whether the pressure P5 is less than the pressure P3. As shown by a block 624, if the pressure P5 is greater than the pressure P3, the processor is operative to successively drive the pumping piston step by step fully into the pumping chamber and to write the corresponding A/D reading into RAM. The processor is operative to compare the pressure reading for each step to the maximum occlusion value specified in the C4 command byte 484 (FIG. 14) to determine whether the patient line is occluded. If the line is occluded, the processor is operative to alarm if the pressure doesn't drop within a predetermined time interval, for example, 30 seconds. The processor is then operative to close the input and output valves as shown by a block 626. As shown by a block 628, the processor is then operative to withdraw the pumping piston and write A/D reading into RAM. The processor then steps the pumping piston into the pumping chamber incrementally by steps of the stepper motor and writes the A/D reading into RAM. The processor is operative to repeat this process until the measured pressure equals the matching pressure P3 and stores that rotary position of the pumping piston stepper motor designated $N_2$ in RAM where the measured pressure equals the pressure P3. As shown by a block 630, the processor is then operative to drive the pumping piston fully into the pumping chamber and to open the patient output line valve as shown by a block 632.

If the pressure P5 is less than the pressure P3, the processor is operative to successively drive the pumping piston almost fully into the pumping chamber, and to write the corresponding A/D reading into RAM. The processor is operative to compare the pressure reading for each step to the maximum occlusion value specified in the C4 command byte 484 (FIG. 14) to determine whether the patient line is occluded. If the line is occluded, the processor is operative to alarm if the pressure doesn't drop within a predetermined time interval, for example, 30 seconds. The processor is then operative to close the input and output valve as shown by a block 636. As shown by a block 638, the processor is then operative to incrementally drive the pumping piston step by step into the pumping chamber and to write the corresponding A/D reading in RAM. The processor continues the process until the measured pressure is equal to the matching pressure P3 and stores the rotary position of the stepper motor at which the measured pressure equals the pressure P3 designated $N_1$ in RAM. As shown by a block 640, the processor is then operative to return the piston to the position of the stepper motor in the block 634, and to open the patient output line as shown by a block 642. The processor is then operative to drive the piston fully into the pumping chamber to pump the corresponding fluid into the patient output line as shown by a block 644.

Figure 19:
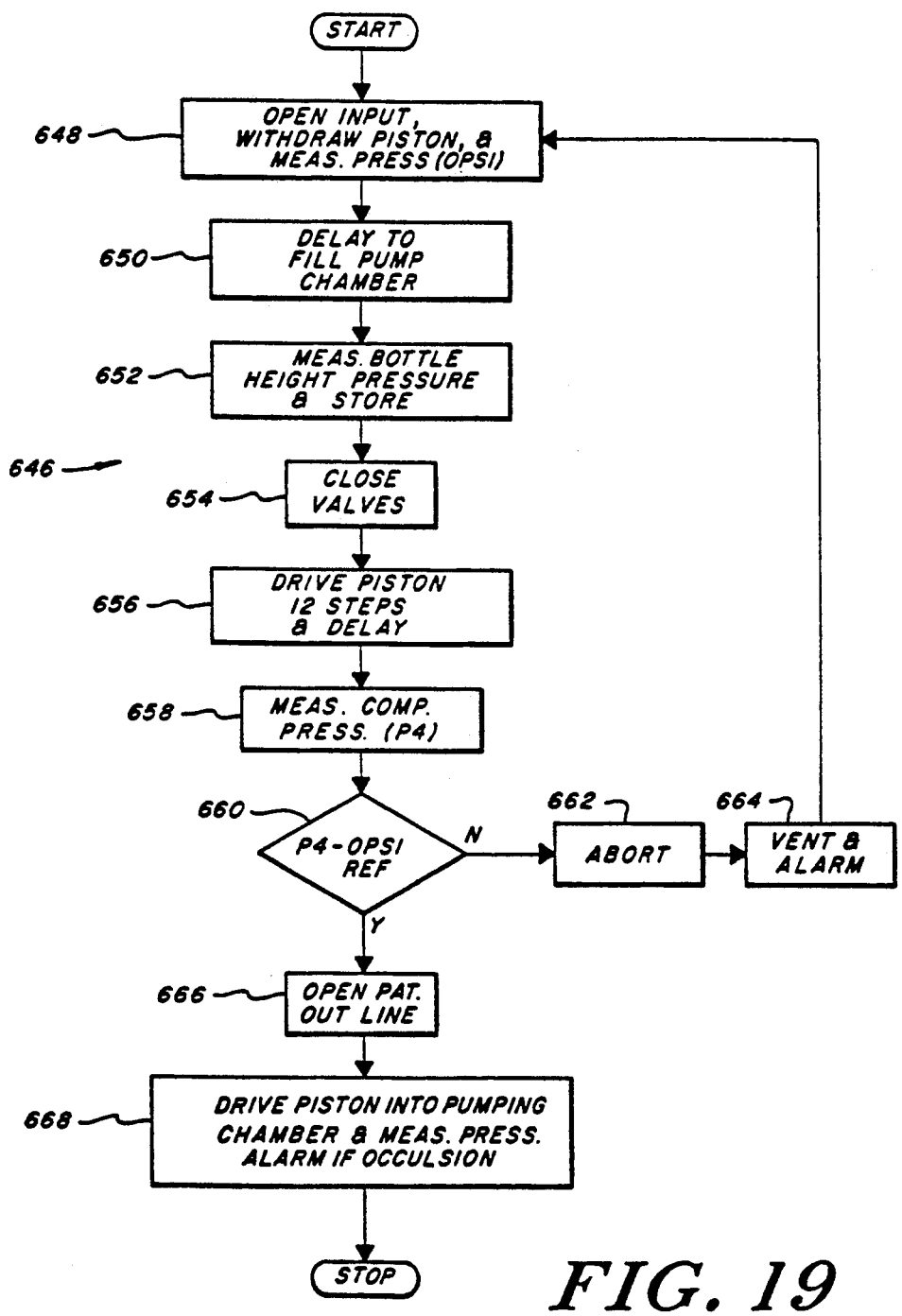
FIG. 19 is a flow chart illustrating another pumping sequence of the pump control processor of the infusion system having plural fluid input ports and at least one patient output port according to the present invention.

Referring now to FIG. 19, generally designated at 646 is a flow chart illustrating another exemplary pumping sequence of the pump control processor. The sequence 646 is preferably employed to pump infusate at comparatively higher operator selected rates of flow. The flow chart 646 is similar to the flow chart 592 (FIG. 18) except that the processor is operative to skip some of the patient pressure monitoring steps of the flow chart of FIG. 18 to allow for faster pumping rates. As described above, the particular pumping sequence is specified by the state of the 13, 14, and 15 bits of the bit field of the $C_1$ command byte, and that the processor can be instructed to do several cycles of the pumping sequence illustrated in FIG. 19 followed by a sequence of the pumping sequence illustrated in FIG. 18 repetitively. As shown by a block 648, the processor is operative to open a selected fluid input port valve, to withdraw the pumping piston, and to write the A/D reading of the pressure transducer into the $D_3$ data byte. The processor is then operative to wait to allow the pumping chamber to fill with fluid from the selected fluid input port as shown by a block 650. The processor is then operative to write the A/D reading of the pressure transducer into the $D_0$ data byte as shown by a block 652. As shown by a block 654, the processor is then operative to close the fluid input and output port valves and then to drive the pumping piston a preselected distance into the pumping chamber, preferably twelve steps, and to delay as shown by a block 656. The processor is then operative to write the A/D reading of the pressure transducer into RAM to measure the compliance pressure for determining air in line as shown by a block 658.

As shown by a block 660, the processor is then operative to determine whether the compliance pressure minus the 0 PSI pressure is greater than the preselected maximum compliance pressure to determine whether there is air in line. As shown by a block 662, if there is air in line, the processor is operative to abort the current pumping sequence, to vent air from the line, to alarm as shown by a block 646 if air remains in the line preferably for three consecutive measurements, and processing for each measurement is returned to the block 648. As shown by a block 666, if no air is in the line, the processor is operative to open the patient output line. The processor is then operative to drive the pumping piston into the pumping chamber and write the A/D reading into RAM. If the pressure is greater than the maximum occlusion pressure, the processor is operative to alarm as shown by a block 668.

Figure 20:
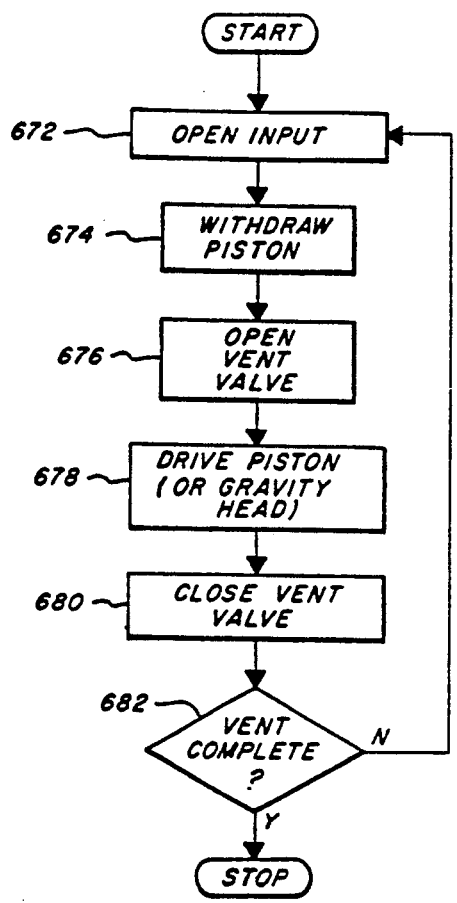
FIG. 20 is a flow chart illustrating another pumping sequence of the pump control processor of the infusion system having plural fluid input ports and at least one patient output port according to the present invention.

Referring now to FIG. 20, generally designated at 670 is another pumping sequence of the pump control processor. The sequence 670 is preferably employed to vent air from the fluid flow path as described above in connection with the description of FIGS. 18 and 19. As shown by a block 672, the processor is operative to open the preselected fluid input port to be used for venting. The processor is then operative to withdraw the pumping piston out of the pumping chamber to allow the fluid to fill into the pumping chamber as shown by a block 674. The processor is then operative to open the vent valve as shown by a block 676 and to drive the pumping piston into the pumping chamber to clear air from the fluid path as shown by a block 678. As shown by a block 680, the processor is then operative to close the vent valve. It will be appreciated that air may also be removed from the fluid flow path by the pressure of the gravity head without driving the piston into the pumping chamber.

Figure 21:
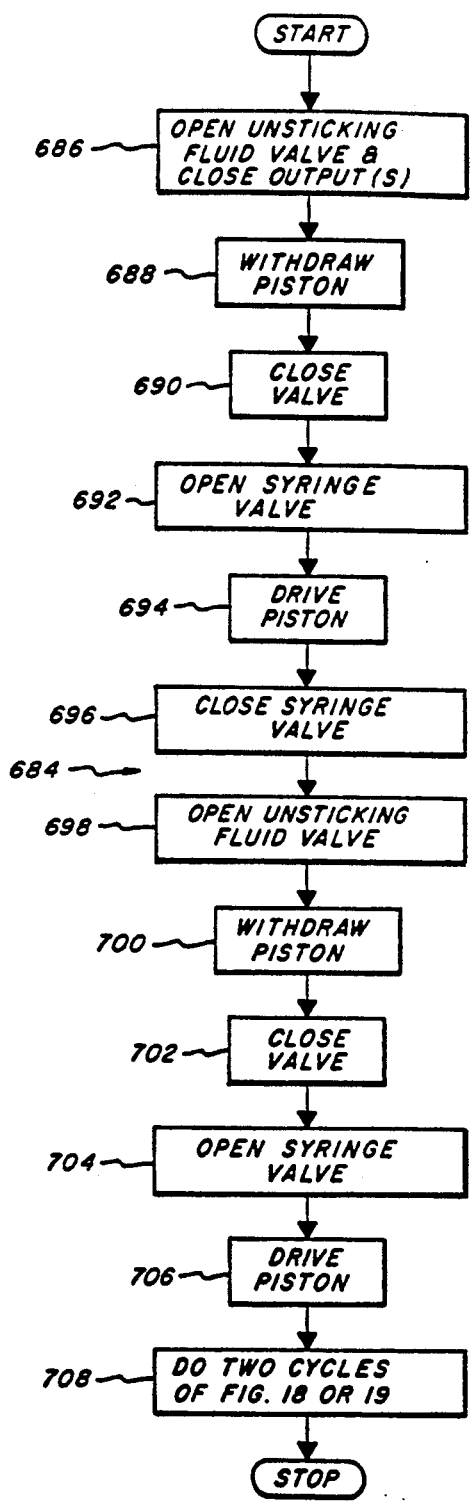
FIG. 21 is a flow chart illustrating another pumping sequence of the pump control processor of the infusion system having plural fluid input ports and at least one patient output port according to the present invention.

Referring now to FIG. 21, generally designated at 684 is a flow chart illustrating another exemplary pumping sequence of the pump control processor. The sequence 684 is preferably employed to unstick the plunger of a syringe fluid input. As shown by a block 686, the processor is operative to open the valve of the fluid port preselected as the unsticking fluid port and to withdraw the pumping piston to allow the unsticking fluid to flow into the pumping chamber as shown by a block 688. The processor is then operative to close the unsticking fluid valve as shown by a block 690 and to open the fluid input having the syringe as shown by a block 692. The processor is then operative to drive the pumping piston into the pumping chamber as shown by a block 694. The expelled fluid is thereby pumped through the cassette and into the syringe to unstick the plunger. The processor is then operative to close the syringe valve as shown by a block 696 and then to open the unsticking fluid valve as shown by a block 698. The processor is then operative to withdraw the pumping piston out of the pumping chamber to allow the unsticking fluid to flow into the pumping chamber as shown by a block 700. The processor is then operative to close the unsticking fluid valve as shown by a block 702 and to open the syringe valve as shown by a block 704. The processor is then operative to drive the pumping piston into the pumping chamber to once again displace fluid therefrom into the syringe to unstick its plunger as shown by a block 706. The processor is then operative to do two cycles from the syringe to remove the fluid pumped thereinto to unstick the syringe plunger as shown by a block 708.

Figure 22:
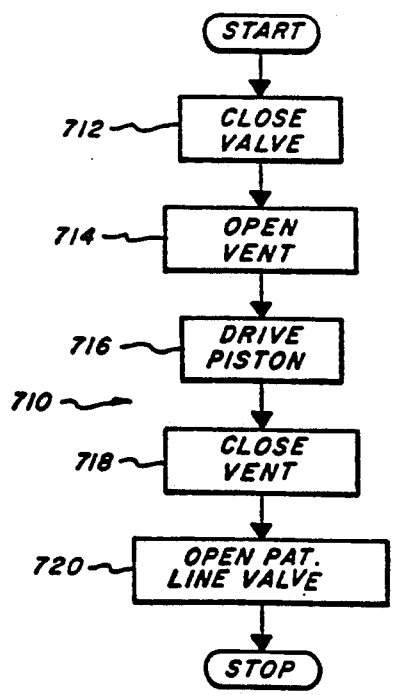
FIG. 22 is a flow chart illustrating another pumping sequence of pump control processor of the infusion system having plural fluid input ports and at least one patient output port according to the present invention.

Referring now to FIG. 22, generally shown at 710 is another exemplary pumping sequence of the pump control processor. The sequence 710 is preferably employed to abort a pumping sequence as described above in a connection with the description of FIGS. 18 and 19. As shown by a block 712, the processor is operative to close the fluid input and patient line output port valves and to open the vent valve as shown by a block 714. The processor then operative to drive the piston into the pumping chamber as shown by a block 716. The processor is then operative to close the vent valve as shown by a block 718 and to open the patient output line valve as shown by a block 720.

Returning now to FIG. 16, as shown by a block 722, the system I/O and pump control processor is then operative to read the status and data information compiled by the pump processor during the pumping sequences described above and write it back to the data file. The processor is then operative to strip off the $D_0$ through $D_5$ data bytes as shown by a block 724. As shown by a block 726, the processor is operative to adapt the desired volume to the actual volume preferably according to the following relations, $$VOL_{eff} = V_0 - A(100 - N2) \qquad 1.$$

$$VOL_{eff} = V_0 - A(88 - N1) \qquad 2.$$

where $V_0$ is the volume of the pumping chamber, A is the volume displaced from the pumping chamber per step, 100 represents the total number of steps of the stepper motor of a pumping sequence, 88 refers the rotary position where the pumping piston is driven almost completely into the pumping chamber as described above in connection with block 634 (FIG. 18), and N1 and N2 are determined as described above in connection with blocks 628, 638 (FIG. 18).

As shown by a block 728, the processor is operative if the status information written into the data file indicates any of the several error and alarm conditions to select the corresponding display template as shown by a block 730, to display it on the operator display as shown by a block 732, and to generate the appropriate audible and visual alarms as shown by a block 734. As shown by a block 736, if any of the explain, history, mute or status keys are depressed, the processor is operative to select the appropriate display template as shown by a block 730 and to display it on the operator interactive display as shown by the block 732.

Figure 23:
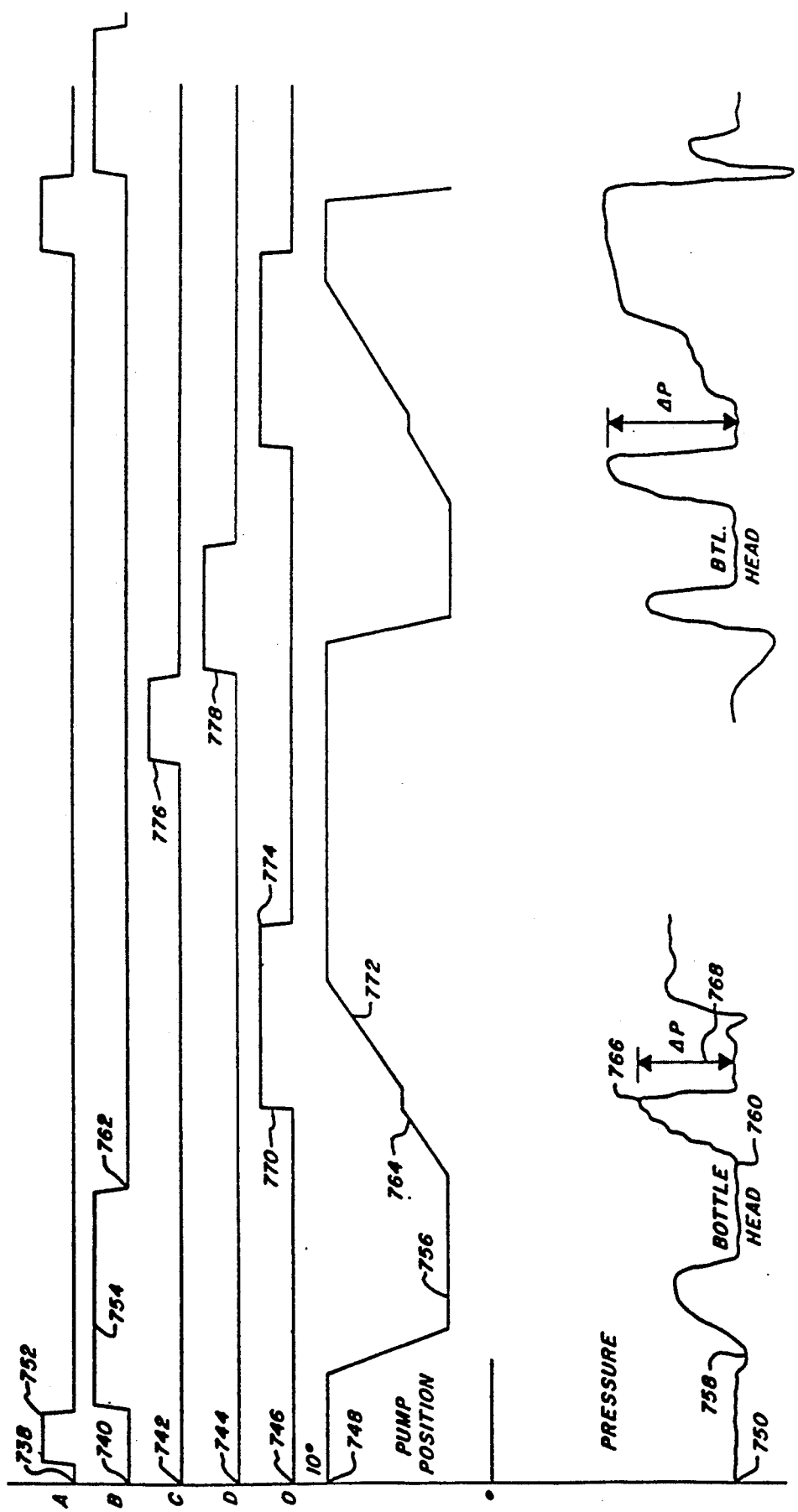
FIG. 23 is a diagram illustrating an exemplary operating sequence of the infusion system having plural fluid input ports and at least one patient output port according to the present invention.

Referring now to FIG. 23, generally designated at 626 is a diagram illustrating an exemplary operating sequence of the infusion system having plural fluid input ports and at least one patient output port according to the present invention. The sequencing diagram 626 illustrates pumping from the "B" fluid input port, and then pumping from the "D" fluid input port, utilizing the pumping sequence of FIG. 19, although it will be appreciated that any other valve order and pumping sequence is a variation of that specifically illustrated in FIG. 23. A line 738 illustrates the state of actuation of the "A" input valve, a line 740 illustrates the state of actuation of the "B" fluid input port, a line 742 illustrates the state of actuation of the "C" fluid input valve, and a line 744 illustrates the state of actuation of the "D" fluid input port value. A line 746 illustrates the state of actuation of the output valve designated "O" and a line 748 illustrates the rotary position of the pump plunger stepper motor during the exemplary sequence. A line 750 illustrates the reading of the pressure transducer.

The pump processor is operative to rotate the valve stepper motor through the open position 752 of the "A" port and stops at the open position 754 of the "B" port. With the "B" valve in the open condition as the pumping piston is withdrawn as illustrated at 756, fluid flows from the "B" fluid input port into the cassette and through the longitudinally extending fluid passageway thereof into the pumping chamber. The processor is operative to take the A/D reading of the pressure transducer to measure the 0 PSI value as shown at 758. After sufficient delay to allow filling of the pumping chamber, the processor is operative to take a reading from the analog to digital converter as shown at 760 to measure the bottle height pressure. The processor is then operative to close the "B" fluid input port as shown at 762. The pump processor is then operative to controllably push the pumping piston into the pumping chamber by rotating the pump stepper motor preferably 12 steps as illustrated at 764. The pump processor is then operative to take the reading of the analog to digital converter with the pumping plunger partially into the pumping chamber to measure the corresponding pressure as illustrated at 766. The change in pressure 768 is indicative of air-in-line and is stored in the appropriate data byte. Assuming for the exemplary sequence that no air is in line, the processor is then operative to rotate the valve stepper motor to open the output valve as illustrated at 770 and to rotate the pump stepper motor to controllably displace the piston into the pumping chamber as illustrated at 772. The processor is operative to take the A/D reading during pumping and to alarm if there is an occlusion situation, not illustrated. The processor is then operative to rotate the valve stepper motor to close the output valve as shown at 774, and to repeat the cycle until the desired volume of fluid is administered into the patient through the "B" input port. At the appropriate time, the processor is then operative to rotate the valve stepper motor through the open position of the "C" port as shown at 776 to the open position 778 of the "D" port to commence a pumping sequence through the "D" fluid input port. The above cycle is then repeated for the "D" port but is omitted for brevity of explication.

It will be appreciated that many modifications of the presently disclosed invention will be apparent to those skilled in the art without departing from the scope of the appended claims.

What is claimed is:

1. An infusion system for infusing fluids into a patient comprising:
   a housing;
   a controller within the housing for control of an infusion through selectable plural fluid input channels;
   a disposable cassette structure releasably mounted to the housing and having:
      a fluid input port and a fluid output port;
      a first rigid portion having at least one surface, a fluid channel recessed in the surface and extending from the input port to the output port, a pump chamber, and a pressure chamber integrally formed in the fluid channel;
      a second rigid portion attached to the first rigid portion over the surface; and
      a resilient diaphragm disposed between the first and second rigid portions to overlay the fluid channel, and including a first portion over the pump chamber and a second portion over the pressure chamber; and
   a pressure sensing member operatively connected to the controller and mounted in alignment with the pressure chamber to sense pressure variations in the pressure chamber.

2. The infusion system of claim 1, wherein the pressure chamber is located downstream from the pump chamber.

3. The infusion system of claim 1, wherein the housing includes means for retaining the first and second rigid portions to the housing.

4. The infusion system of claim 1, wherein the retaining means comprises a flange member.

5. The infusion system of claim 1, further comprising means for preventing collapse of the resilient diaphragm into contact with an opposed face of the pressure chamber.

6. An infusion system for infusing fluid from plural sources into a patient comprising:
- a plurality of fluid input channels for each receiving a selected infusate from a corresponding one of plural sources;
- a pump for pumping fluid through each input channel to the patient;
- a controller for selectively controlling parameters of rate, volume, and duration of pumping for each of the channels in any order, the controller including means for generating a status signal representative of status of each channel including: pumping at a programmed rate; pumping stopped; and pumping at a keep-vein-open rate, the controller further including means for including in the status signal a signal representative of the rate of pumping for each channel;
- a valve corresponding to each input channel and formed in a disposable controller-mounted cassette the valve selectably opened and closed by the controller according to rate, volume, and duration of pumping in the corresponding channel;
- a display operatively connected to the controller; and
- the controller further including means for sending the status signal representative of the status of each channel and the rate of pumping for each channel to the display for display thereon.

7. The infusion system of claim 6 wherein the rate of pumping display portion displays rate of pumping in milliliters per hour.

8. An infusion system for infusing fluids into a patient comprising:
- plural fluid input flow channels respectively connected to plural sources of fluids intended for infusion to a patient;
- a housing having a pump actuator for pumping fluid along an infusion path from a selectable fluid source to the patient through the corresponding fluid input flow channel;
- the infusion path being defined by a disposable cassette structure releasably and lockably mounted on the housing for interactive cooperation therewith, the cassette structure comprising at least one first wall defining at least one recess and a second wall confronting the recess to define an enclosed space and including a resilient diaphram disposed to overlay said recess in fluid communication with the infusion path;
- a controller operable to control the rate, volume, and duration of pumping along the plural input flow channels and along the cassette-defined infusion path to provide controlled flow in any one thereof;
- said controller adapted for pressure monitoring in the enclosed space;
- means for detecting alarm conditions in response to pressure monitors, the alarm conditions including at least one of an occlusion in the infusion path, air in the infusion path, and failure of proper mounting and locking to the housing; and
- means for generating an alarm signal in response to the detection of an alarm condition.

9. The infusion system of claim 8, wherein the alarm condition detecting means includes means for sending a signal representative of the type of alarm condition to the controller, and the controller is responsive to control the pumping along the infusion path as a function of the alarm condition.

10. An infusion system for infusing plural fluids into a patient along a plurality of input channels comprising:
- a unitary housing;
- a unitary controller disposed within the housing for controlling the infusion along a plurality of input channels;
- a first pump portion integral to said housing and operatively connected to the controller for pumping fluid to be infused from one of the channels along an infusion flow path to the patient;
- a disposable cassette releasably mounted to the housing, comprising a second pump portion cooperative with the first pump portion, at least a portion of the infusion flow path being disposable cassette-located;
- at least one cassette-located valve operatively connected to the controller for enabling and disabling flow through a corresponding input channel to the infusion flow path;
- the valve and the pump portions being controlled by the controller to control flow parameters including rate of pumping, duration of pumping, and volume of fluid to be pumped through the cassette; and
- means for providing operator selection of at least one of the parameters for each input channel through the controller.

11. An infusion system for infusing fluids into a patient comprising:
- a housing;
- a controller within the housing for control of an infusion through selectable plural fluid input channels;
- a fluid input port and a fluid output port disposed for directing fluid through the housing;
- a first disposable rigid portion having at least one surface, a fluid channel recessed in the surface and extending from the input port to the output port, a pump chamber, and a pressure chamber integrally formed in the fluid channel;
- a second disposable rigid portion attached to the first rigid portion over the surface, the first and second rigid portions being releasably mounted to the housing;
- a resilient disposable diaphragm located between the first and second rigid portions to overlay the fluid channel, and including a first portion over the pump chamber and a second portion over the pressure chamber;
- a pump actuator member operatively connected to the controller and disposed within the housing in alignment with the pump chamber to control pumping through the fluid channel; and
- a pressure sensing member operatively connected to the controller and disposed within the housing in alignment with the pressure chamber to sense pressure variations in the pressure chamber.

* * * * *

UNITED STATES PATENT AND TRADEMARK OFFICE
CERTIFICATE OF CORRECTION

PATENT NO. : 5,304,126
DATED : April 19, 1994
INVENTOR(S) : Paul Epstein et al

It is certified that error appears in the above-indentified patent and that said Letters Patent is hereby corrected as shown below:

Column 11, line 24, "key 150 when" should read --key 150, a stop key 152, an override key 154, and a priming key 156. The start key--.

Signed and Sealed this

Eighth Day of November, 1994

Attest:

BRUCE LEHMAN

Attesting Officer  Commissioner of Patents and Trademarks